United States Patent
Crane et al.

(10) Patent No.: US 9,097,687 B2
(45) Date of Patent: Aug. 4, 2015

(54) SENSOR CALIBRATION

(75) Inventors: Barry Crane, Oxfordshire (GB); Ian Francis, Oxfordshire (GB); Robert Perkins, Oxfordshire (GB); William Paterson, Oxfordshire (GB)

(73) Assignee: Lightship Medical Limited, London (GB)

( * ) Notice: Subject to any disclaimer, the term of this patent is extended or adjusted under 35 U.S.C. 154(b) by 11 days.

(21) Appl. No.: 13/430,066

(22) Filed: Mar. 26, 2012

(65) Prior Publication Data

US 2012/0240656 A1    Sep. 27, 2012

Related U.S. Application Data

(63) Continuation of application No. 12/308,865, filed as application No. PCT/GB2007/002414 on Jun. 28, 2007, now Pat. No. 8,141,409.

(30) Foreign Application Priority Data

Jun. 28, 2006  (GB) .................................. 0612834.2

(51) Int. Cl.
*G01N 35/00* (2006.01)
*A61B 5/1459* (2006.01)
(Continued)

(52) U.S. Cl.
CPC ........ *G01N 35/00693* (2013.01); *A61B 5/1459* (2013.01); *A61B 5/1495* (2013.01); *A61B 5/14546* (2013.01); *G01N 27/3274* (2013.01); *A61B 5/14532* (2013.01)

(58) Field of Classification Search
USPC ............................. 73/1.02, 61.59; 436/8, 14
See application file for complete search history.

(56) References Cited

U.S. PATENT DOCUMENTS 3,202,273 A * 8/1965 Riall ............................. 206/63.3
4,689,308 A * 8/1987 Gerhard .......................... 436/18
(Continued)

FOREIGN PATENT DOCUMENTS

DE     195 46 535     6/1997
JP     61-270650      11/1986
(Continued)

OTHER PUBLICATIONS

Written Opinion of the International Searching Authority for PCT/GB2007/002414, mailed Oct. 29, 2007.
(Continued)

*Primary Examiner* — Paul West
(74) *Attorney, Agent, or Firm* — Fish & Richardson P.C.

(57) ABSTRACT

A sensor kit comprising a sensor for detecting an analyte, a sensor housing and a calibration chamber. The calibration chamber comprises a first compartment containing a first calibration solution and a second compartment containing a source of the analyte to be detected. A dividing material is located between the first and second compartments enabling them to be mixed on breakage or removal of the dividing material. Further compartment(s) containing further source(s) of the analyte may optionally be provided. Calibration can carried out by (a) taking a reading of the analyte concentration of the first calibration solution, (b) mixing the contents of the first and second compartments by breaking or removing the dividing material, and (c) taking a reading of the analyte concentration of the resulting mixture. Steps (b) and (c) can be repeated for further compartment(s) to provide further reading(s) if desired.

13 Claims, 14 Drawing Sheets

(51) Int. Cl.
*A61B 5/1495* (2006.01)
*G01N 27/327* (2006.01)
*A61B 5/145* (2006.01)

(56) References Cited

U.S. PATENT DOCUMENTS

| | | |
|---|---|---|
| 5,114,859 A | 5/1992 | Kagenow |
| 5,156,972 A | 10/1992 | Issachar |
| 5,188,803 A | 2/1993 | Hochberg |
| 5,208,147 A * | 5/1993 | Kagenow et al. ............... 435/14 |
| 5,992,211 A | 11/1999 | Skrtic |
| 6,037,178 A | 3/2000 | Leiner et al. |
| 7,785,535 B2 | 8/2010 | Chen et al. |
| 2003/0224523 A1 | 12/2003 | Thornberg et al. |
| 2004/0126766 A1* | 7/2004 | Amorese ........................ 435/6 |
| 2006/0108218 A1 | 5/2006 | Gephart et al. |

FOREIGN PATENT DOCUMENTS

| | | |
|---|---|---|
| JP | 63-247646 | 10/1988 |
| WO | WO 85/04719 | 10/1985 |
| WO | WO 90/02938 | 3/1990 |
| WO | WO 93/03362 | 2/1993 |
| WO | WO 94/19683 | 9/1994 |
| WO | WO 01/67079 | 9/2011 |

OTHER PUBLICATIONS

Search Report for Co-pending Great Britain Application No. GB0612834.2, dated Oct. 25, 2006, 1 page.
Japanese Office Action, in Application No. JP 2009-517398, dated Jul. 25, 2011, 6 pages.

* cited by examiner

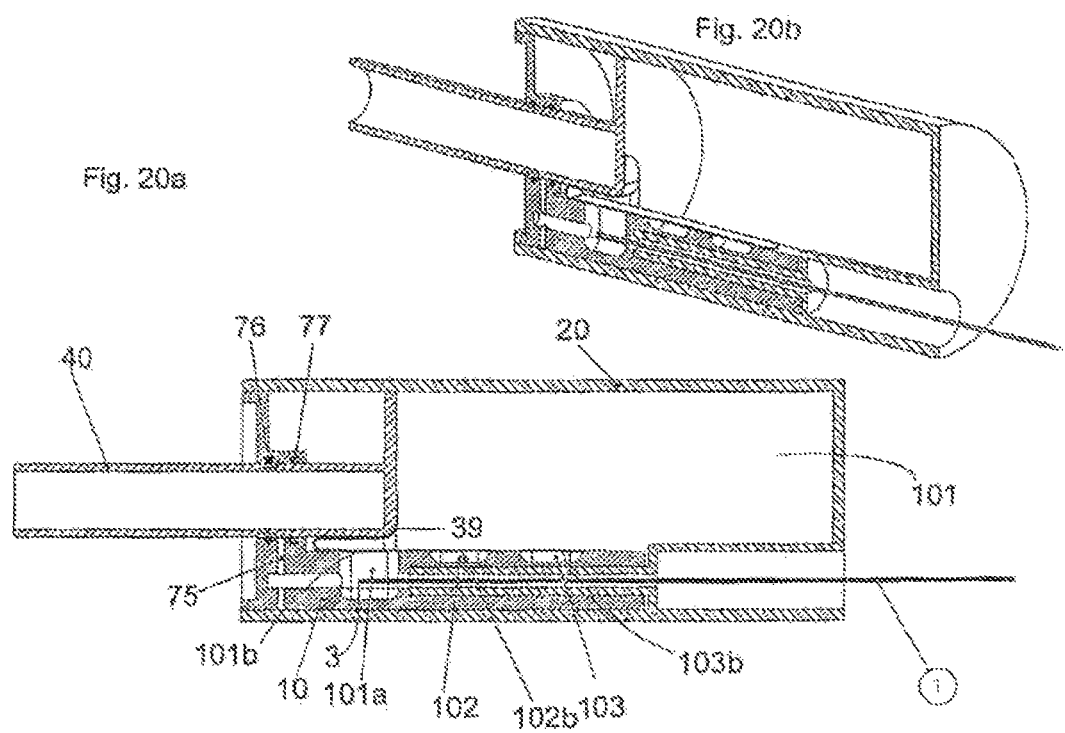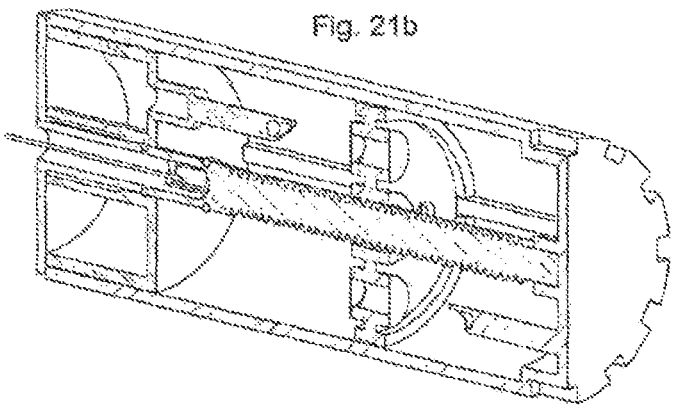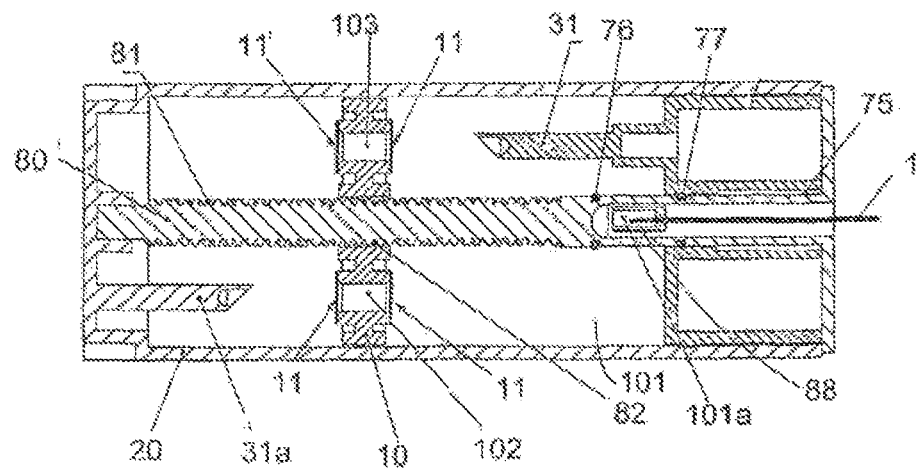

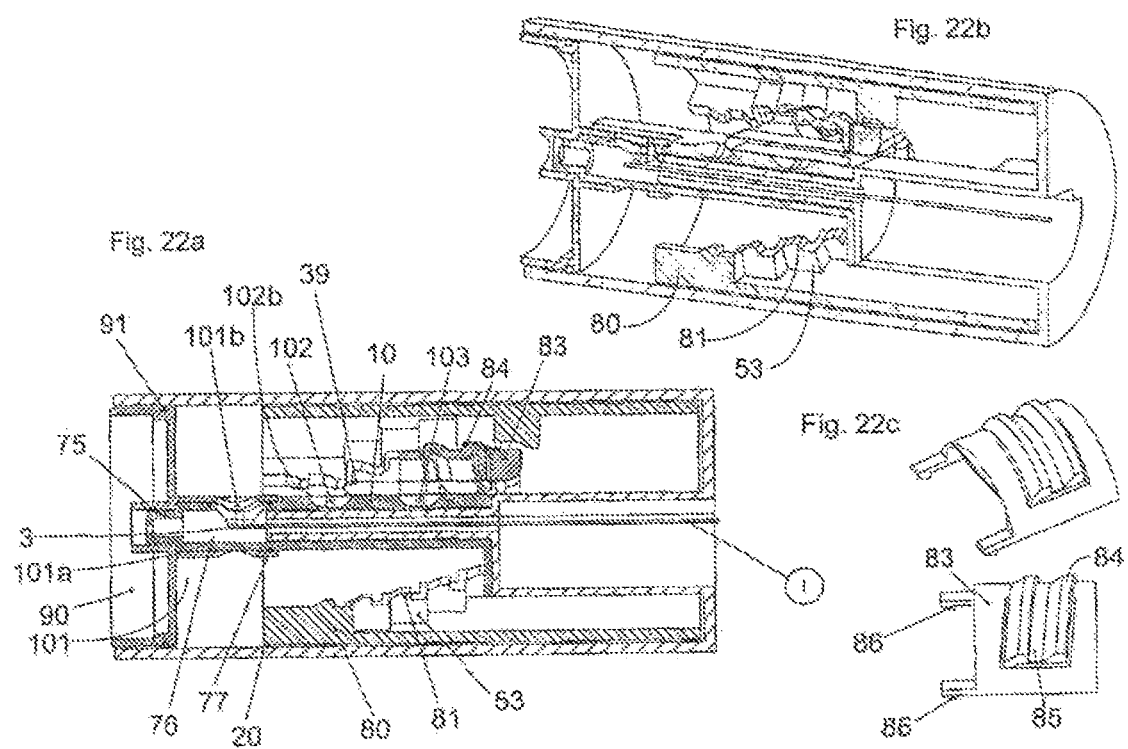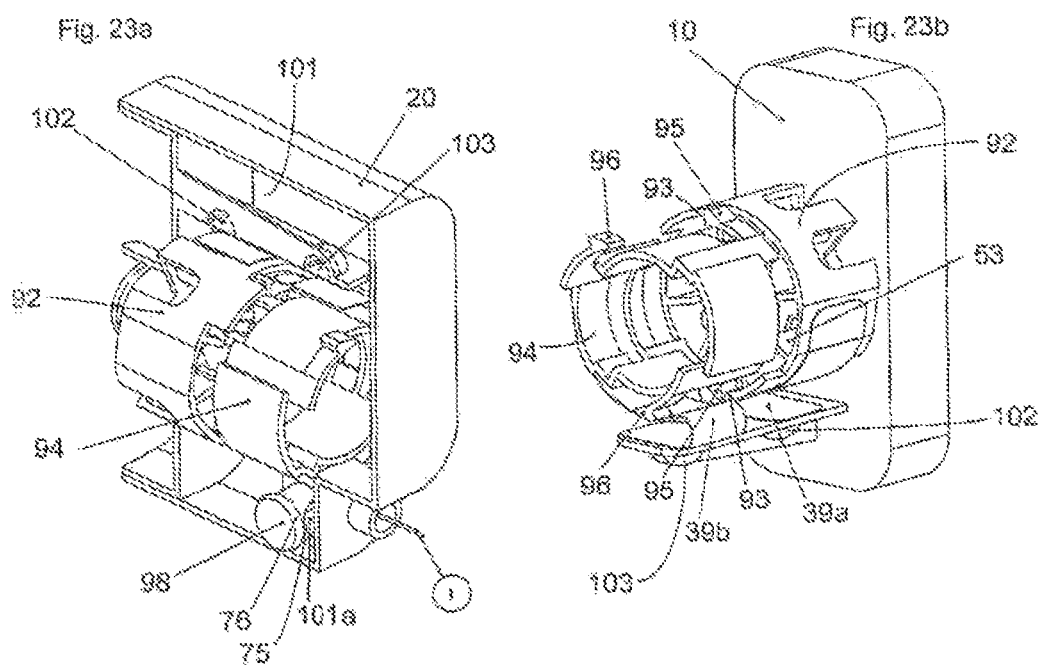

SENSOR CALIBRATION

CROSS-REFERENCE TO RELATED APPLICATIONS

This application is a continuation of and claims priority under 35 U.S.C. §120 to Ser. No. 12/308,865, filed on Mar. 11, 2009, which is a National Stage application under 35 U.S.C. §371 and claims benefit under 35 U.S.C. §119(a) of International Application No. PCT/GB2007/002414, having an International Filing Date of Jun. 28, 2007, which claims the benefit of Application No. 0612834.2 filed on Jun. 28, 2006.

FIELD OF THE INVENTION

The present invention relates to a sensor kit including a sensor for detecting an analyte and a calibration chamber to enable calibration of the sensor. A method for sterilising the kit, and a method for calibrating the sensor are also described. The invention relates in particular to invasive or implantable sensors which are required to be sterile. However, sensors used in other applications where sterility is an advantage, e.g. to prevent biodegradation of certain contained reagents, are also envisaged.

BACKGROUND TO THE INVENTION

The usual aim in developing a chemical sensor or biosensor is to produce a digital electronic signal, which is proportional to the concentration of a specific chemical or set of chemicals (analyte). The sensor usually comprises two main components, a chemical or biological part that reacts or complexes with the analyte in question (ideally specifically) to form new chemical or biological products or changes in energy that can be detected by means of the second component, a transducer. The chemical/biological component can be said to act as a receptor/indicator for the analyte. A variety of transduction methods can be used including electrochemical (such as potentiometric, amperometric, conductimetric, impedimetric), optical, calorimetric and acoustic. After transduction the signal is usually converted to an electronic digital signal.

Since the signal generated by the chemical/biological reaction with the analyte is usually dependent not only on the concentration of the analyte but also on the characteristics of the sensor itself, such sensors usually require calibration before they can be utilised quantitatively. The way in which the signal varies with the analyte concentration determines the shape of the calibration curve (signal versus analyte concentration) and may define the number of calibration points. Typical calibration curves can be straight line, exponential, s-shaped etc. and the principal of calibration applies to all methodologies of transduction for chemical or biological sensors.

Calibration of sensors with an invasive medical application has its own set of specific issues. Invasive or implantable medical sensors must be presented to the patient in a sterile condition, and are often single use, disposable devices. Ideally, the sensor should be calibrated just before its use since some sensor characteristics that can affect the calibration curve vary with time (ageing effect). It is often the case that the time between sensor manufacture and use can be many months, so calibration at the point of manufacture can lead to inaccuracies in the end result. This means that the attendant clinician or nurse will be required to perform the calibration whilst maintaining sterility of the sensor. Additional constraints applied by the clinician/nurse are that the calibration process should be simple to perform, ideally invisible to the person performing the calibration, and be quickly completed (preferably in less than 10 minutes).

Calibration of many currently available medical sensors requires the clinician/nurse to carry out a number of specific steps which can lead to errors or inaccuracies in the measurement if the process is not followed correctly. There is therefore a need for a more simple calibration process, useful in connection with any invasive or implantable device, which fulfills the above discussed requirements.

Sterilization of such devices can also provide difficulties. The sterilisation process is typically carried out at the point of manufacture to avoid difficulties with poor or incomplete sterilisation procedures at a hospital or clinic, and to save time on behalf of the clinician or nurse. Three forms of sterilisation are commonly used for the sterilisation of medical devices: steam, irradiation, and ethylene oxide. Steam is usually used for metal surgical instruments, bandages and liquids within containers but is not appropriate for devices with low melting plastic components or labile chemical or biological components since steam sterilisation usually takes place at temperatures above 116 C. Irradiation, usually gamma irradiation, is a penetrating means of sterilisation and can therefore sterilise liquids in containers but can degrade many plastics, chemicals and biological materials. This degradation is most likely to occur in the presence of water and oxygen. Ethylene oxide sterilisation is a surface sterilant that generally does not degrade the receptor and other materials that comprise a sensor, but should only be used to sterilise materials that are free from significant amounts of water, since the ethylene oxide can react with the water to form ethylene glycol. Thus ethylene oxide is the preferred means of sterilising chemical sensors.

Ethylene oxide sterilization, however, has a number of drawbacks. Firstly, it is usual in sensor construction to immobilise the receptor to the transducer and this is usually achieved by the utilisation of polymeric materials. If the sensor is to measure water-soluble analytes, and analytes soluble in blood plasma, the polymeric immobilisation material must be hydrophilic (readily adsorb water) to allow the diffusion of the analyte through the immobilisation material to the receptor material and allow measurement to take peace. To sterilise such a sensor with ethylene oxide, all water must be removed from the hydrophilic material prior to sterilisation.

Secondly, to calibrate a sensor that is to measure a water-soluble analyte at the point of use, the user must immerse the sensor in water based solutions of the analyte (or analogues of the analyte) whilst maintaining sterile integrity. However, a calibration vessel, containing calibration solution(s), cannot be sterilised with ethylene oxide, which is a surface sterilant, and therefore must be sterilised by heat or preferably irradiation. The calibration solution(s) are therefore typically provided in separately sterilised packaging from the sensor. During calibration, sterility may be lost due to the need to break these packages to carry out the calibration process.

There is therefore also a need for a means of calibrating a sensor which avoids loss of sterility during calibration.

SUMMARY OF THE INVENTION

The present invention provides a sensor kit comprising:
(i) a sensor for detecting an analyte, said sensor having a sensing region comprising a receptor for said analyte;
(ii) a sensor housing containing said sensor, at least a part of said sensor housing being penetrable by water or aqueous solutions; and (iii) a calibration chamber, said calibration chamber comprising at least a first and a second compartment, the first compartment containing a first calibration solution comprising water or an aqueous solution and the second compartment containing a source of said analyte, said first and second compartments being separated by a water-impermeable dividing material.

Also provided is a calibration chamber for the kit of the invention, and a method of calibrating a sensor contained within the kit. The calibration method comprises:

(i) optionally exposing the sensing region of the sensor to the first compartment of the calibration chamber so that the first calibration solution in the compartment is in contact with the sensing region;

(ii) determining the sensor output (i.e. the measured concentration of analyte) for the first calibration solution;

(iii) breaking or otherwise removing the dividing material of the calibration chamber, to form a second calibration solution comprising a mixture of the first calibration solution and the source of analyte;

(iv) determining the sensor output (i.e. the measured concentration of analyte) for the second calibration solution; and (v) calibrating the sensor using the determined sensor output readings.

In the simplest embodiment of the invention, on receipt by the user the sensing region of the sensor is already located within the first compartment of the calibration chamber such that optional step (i) need not be carried out. However, where this is not the case, the sensing region can easily be exposed to the first compartment, for example by moving the sensor housing so that a piercing tip of the housing pierces an outer wall of the first compartment and housing and sensor enter the first compartment. Alternatively, this may be achieved by breaking a seal or removing a barrier which separates the sensor from the first compartment.

Once the sensing region is exposed to the contents of the first compartment, a reading of the analyte concentration of the solution in the first compartment (the first calibration solution) can be taken. The first compartment typically does not contain any analyte, so this step provides a first reading corresponding to zero analyte concentration.

In a second step, the dividing material is removed or caused to break, thus mixing the contents of the first and second compartments. The source of analyte within the second compartment, containing a known quantity of analyte, will thus be mixed with the water or aqueous solution of the first compartment, providing a second calibration solution having a known concentration of analyte. A second reading of the analyte concentration can then be made. By use of these two readings and a predetermined algorithm, a calibration curve can be generated and the device appropriately calibrated.

This method therefore involves very simple steps and can be completed in a very short period of time, typically in 5 minutes or less. In the case of a manually operated sensor, the simplicity of the method reduces the chances of errors occurring during the calibration process and encourages user compliance. The method is also simple to automate as discussed below.

By the term "breaking" the dividing material, we mean that the dividing material is ruptured or pierced or an opening is made in the dividing material in some way which enables the contents of the first and second compartments to contact each other. By the term "removing" the dividing material, we mean that at least a part of the dividing material is removed, e.g. peeled away, in such a way that the contents of the first and second compartments can contact each other. The particular means by which the dividing material is broken or removed is not particularly limited, as long as it enables the contents of the first and second compartments to contact each other.

All of the steps in the process can be automated. Typically, the sensor is connected to an appropriate detection system, which can be programmed to measure the analyte concentration at regular intervals. In this way, the detection system automatically takes the first reading on connection with the sensor. Following mixing of the contents of the first and second compartments (and these steps may also be machine-driven if desired), the detected concentration will gradually increase as the source of analyte dissolves until it reaches a plateau value. This continuous plateau value forms the second reading.

In a preferred embodiment, the dividing material of the calibration chamber is under tension. This means that piercing the dividing material, for example using the piercing tip of the sensor housing or a separate needle, causes the material to burst, which fully opens up the calibration chamber, rather than merely generating a small pierced hole. This in turn allows easy mixing of the contents of the first and second compartments.

A further preferred embodiment involves a three point calibration. In this embodiment, the calibration chamber includes a second source of the analyte. On mixing of the second source of analyte into the solution, a third calibration solution is generated having a greater concentration of analyte than the first and second solutions. By taking a third reading of the sensor output for this third solution, a third calibration point can be generated. Since a large number of devices require three calibration points in order to be accurately calibrated with a predetermined calibration algorithm, the use of a second source of analyte is preferred.

The second source of analyte may be provided in a third compartment which can be accessed by breaking or removing a dividing material separating the third compartment from the remainder of the calibration chamber. In an alternative embodiment, however, the second source of analyte is contained in the second compartment within a slow release capsule or package. On breakage of the dividing material, the slow release capsule contacts the water or aqueous solution of the first compartment and slowly begins to dissolve. After a certain time lapse, during which the second reading (relating to the second calibration solution) is taken, the slow release capsule dissolves providing a second solubility plateau and hence the third calibration solution. The third reading can then be taken.

This latter embodiment has the particular advantage that very few mechanical steps are required. In the above-described automated process, following taking of the second reading, the detected concentration will once again start to increase as the slow release capsule begins to release its contents. Following complete release and dissolution, a further plateau in the detected concentration will be reached. This concentration forms the third reading. Similarly, four or more point calibrations could equally be achieved by use of additional slow release capsules which release their contents at different time intervals.

The sensor kit of the invention is particularly appropriate for use with invasive or implantable sensors, in particular single use sensors which are provided to the user in sterile form. The kit can be provided to the user in a single, sterile container which can be prepared by the sterilisation method of the invention. This sterilisation method comprises sterilising the calibration chamber, preferably using y-ray irradiation, inserting the pre-sterilised calibration chamber, sensor and sensor housing into the container, sealing the container and sterilising the container, sensor and sensor housing, preferably using ethylene oxide sterilisation.

The calibration chamber forms a separate sealed part, which can therefore be separately sterilised prior to insertion into the container. The method of the invention therefore provides a single sterile package containing sterilised calibration reagents within the calibration chamber. The user may optionally open the sterile container prior to calibration, but the calibration chamber remains sealed thus maintaining sterility during calibration.

In a preferred embodiment, the sensing region of the sensor is exposed to the first compartment of the calibration chamber prior to opening the sealed container. This embodiment has the advantage that the sensing region of the sensor is already contained within the sterile calibration chamber on opening the container, and further avoids loss of sterility during calibration. This can be achieved, for example, by removal of a seal separating the sensor from the first compartment. Alternatively, the sensor housing may be moved from a position outside the first compartment to inside the first compartment, e.g. by pushing on a part of the sensor housing which extends outside the sealed container. Alternatively, a compressible arm is provided in the container, into which the sensor housing extends. By compressing the compressible arm, the sensor housing can be pushed further into the container, thus causing a piercing tip of the sensor housing to pierce the wall of the first compartment of the calibration chamber.

In a preferred aspect of this embodiment, the container includes a guide channel containing the sensor housing, such that when the compressible arm is compressed the sensor housing is moved laterally within the guide channel and into the calibration chamber. Movement of the sensor housing in other directions can thus be minimised.

BRIEF DESCRIPTION OF THE FIGURES

The present invention is further described: below with reference to exemplary embodiments and accompanying drawings in which:

FIG. 19b=position for storage and measurement of first reading of calibration method; FIG. 19c=position for second and optional further readings of calibration method).

FIGS. 20-23 depict structural details of practical examples of a sensor kit of the invention.

DETAILED DESCRIPTION OF THE INVENTION

Sensor

The present invention is appropriate for use with any type of sensor which requires calibration, but is particularly useful for sensors which must be maintained in a sterile condition. This includes sensors for carrying out in vitro testing, whose accuracy may be affected by increased bacterial counts. For example, bacterial presence can influence the pH of a sensor and therefore affect accuracy. However, the present invention is particularly useful for invasive or implantable sensors (hereinafter invasive sensors) which must be maintained in a sterile condition during storage and calibration.

Such invasive sensors include sensors for determining a variety of properties, typically properties of blood, although other tissues may also be subject to sensing Potassium, urea, creatinin and glucose sensors are examples of such invasive sensors. The present invention will be described further with reference to a particular type of invasive glucose sensor, but it should be understood that the invention is not limited to such sensors.

Monitoring of patient glucose levels is particularly useful in intensive care units. It has been found that intensive care patients tend to have very high glucose levels. Mortality rates can be significantly reduced merely by maintaining normal glucose levels by administration of insulin. If, however, the patient is administered too much insulin then there is a risk of hypoglycemia. Intermittent monitoring of glucose is not sufficient to prevent hypoglycemia since the time from sampling to ascertaining a result is generally too long to accurately determine the current status of a patient, and their response to any administered insulin. Further, in vitro intermittent monitoring significantly increases the workload for the nursing staff due to the frequency of testing required. Invasive devices which provide continuous glucose monitoring are therefore particularly useful in the intensive care environment.

Figure 1:
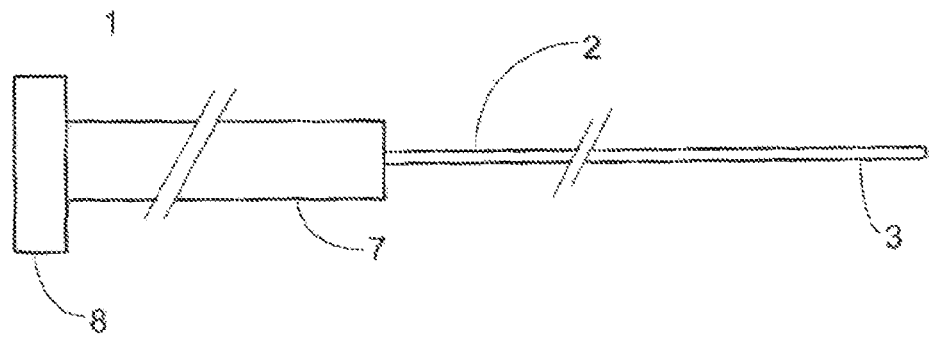
FIG. 1 depicts a sensor for use in the sensor kit of the invention.
Figure 2:
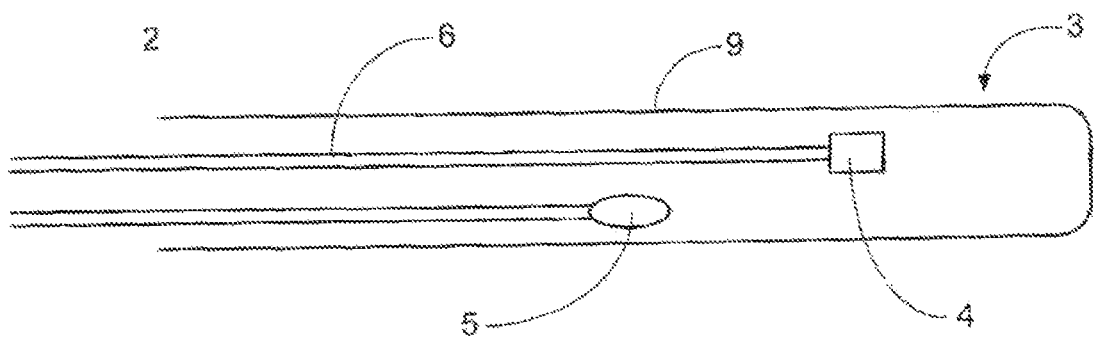
FIG. 2 depicts the sensing region of the sensor of FIG. 1 in more detail.

One particular invasive glucose sensor is based on a fibre optic technique and is depicted in FIG. 1. The sensor 1 comprises an insertable tip 2 which is adapted for insertion into a patient, for example insertion into a blood vessel through a cannular. The insertable tip includes a sensing region 3 (depicted in more detail in FIG. 2) in which the glucose receptor 4, and typically also a temperature sensor 5, are positioned. The glucose receptor is immobilised on or in an optical fibre 6, such that a signal emitted by the receptor is transmitted through the optical fibre. The optical fibre extends through cable 7 to connector 8, which is adapted to mate with an appropriate monitor (not depicted). The monitor typically includes further optical cable that mates with the connector at one end and at the other bifurcates to connect to (a) an appropriate light source for the optical sensor and (b) a detector for the emitted signal. Electrical connection to the temperature sensor is also provided through connector 8 and appropriate detection equipment is provided by the monitor.

The sensing region of the sensor is coated with a membrane 9 which should generally be hemocompatible and allow diffusion of glucose (or other analyte where appropriate) from the surrounding blood or body fluid to the receptor 4.

Receptors for a number of analytes which could be incorporated into such a sensor are known in the art. For example, crown ethers may be used to detect potassium and various enzymes are also useful. In the case of glucose, a useful receptor is a boronic acid compound having a fluorophore. The boronic acid species provides the ability to complex with glucose and the fluorescence emission pattern of the molecule is altered in the presence of glucose, which allows optical detection.

The receptor is typically immobilised to the optical fibre in a hydrogel which allows diffusion of water and glucose to the receptor compound. Cross-linked polyacrylamide or polyhydroxyethylmethacrylate (p-HEMA) are examples of hydrogels that can be used.

Calibration Chamber

A key aspect of the present invention is the calibration chamber, which is provided to enable calibration, typically under sterile conditions, of a sensor such as that described above. The calibration chamber provides the means for obtaining two or more sensor readings for calibration solutions of known analyte concentration. The calibration chamber is typically sealed and pre-sterilised and is designed such that calibration can be performed without damaging the seal or sterility of the chamber.

Embodiment 1

Figure 3A:
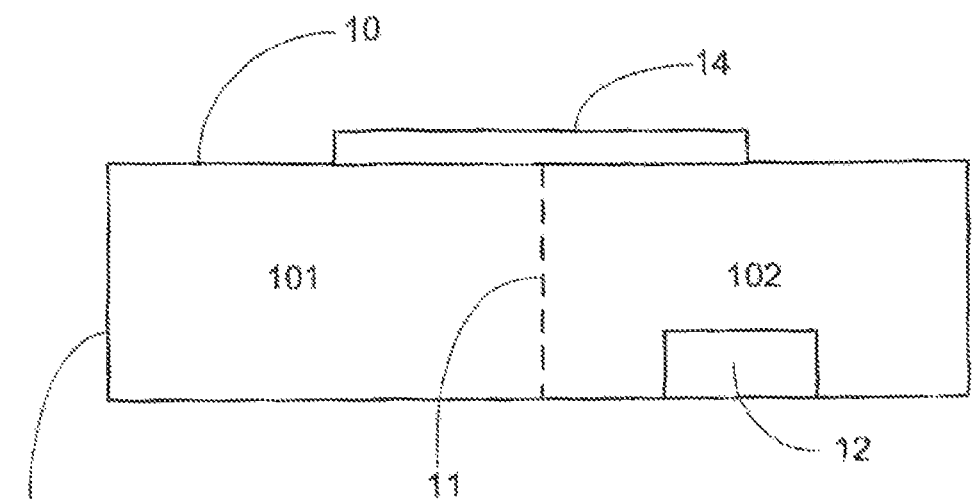
FIGS. 3a to 3c depict embodiments of the calibration chamber of the invention.

A first embodiment of a calibration chamber according to the invention is depicted in FIG. 3a. The calibration chamber 10 comprises two compartments 101 and 102, which are separated by a water-impermeable dividing material 11 e.g. a breakable dividing material. The first compartment 101 contains water or an aqueous solution. Typically, this compartment contains an isotonic solution and does not contain the analyte. Thus, sensing of the analyte concentration in this compartment typically provides a zero reading. However, analyte may be contained in the first compartment, e.g. at low concentration, if desired. Preferably, analyte is only contained in the first compartment if it is not degraded by irradiation in the presence of water.

The second compartment contains a source of the analyte 12, e.g. glucose. This may be in the form of a concentrated solution of the analyte or, as depicted at 12 in FIG. 3a, the analyte itself in solid form. Where the analyte is glucose, the second compartment typically contains glucose in solid form (e.g. powder, tablet etc.), whilst the first compartment does not contain glucose. Aqueous solutions of glucose have been found to degrade on sterilisation with either heat or gamma-radiation. Thus, this embodiment has the advantage that no aqueous solution of glucose is present and degradation is minimised. The second compartment may be under inert gas atmosphere (e.g. dry nitrogen) to avoid oxygen-induced irradiation degradation.

Calibration of the sensor can be carried out by exposing the sensing region of the sensor to the first compartment 101 containing the first calibration solution. In one aspect of this embodiment, the sensing region of the sensor is inserted into the first compartment 101. To enable the sensor to be inserted, outer wall 13 of the first compartment is typically at least in part piercable. For example, the outer wall 13 may be a septum which can be pierced by a needle. The sensor can be inserted into the first compartment through or within the needle. Once the sensing region is in place within the first compartment, a first reading of the sensor output is taken.

In an alternative aspect of this embodiment, a seal is provided between the sensor and the first compartment. Breaking the seal, e.g. by movement of the sensor or a part of the outer wall 13 of the first compartment, causes the content of the first compartment to flow around the sensor, thus exposing the sensor to the first calibration solution.

The dividing material separating first and second compartments is then broken or removed allowing the contents of these compartments to mix. The dividing material is typically broken or removed without opening the sealed calibration chamber in order to maintain sterility. Thus, the material is broken for example by piercing with a needle inserted into the first compartment through the outer wall 13. In a typical embodiment, the sensor is inserted into the first compartment within a needle, and the needle, containing the sensor, can then be pushed forwards to rupture the dividing material.

The dividing material may be any material which can be broken, ruptured or removed causing the contents of the first and second compartments to mix. In one embodiment, the dividing material is an elastomeric material which is maintained under tension so that on piercing with a needle the material will be fully ruptured. Natural or synthetic rubbers are examples of such materials. In an alternative embodiment, the material is rigid, but is scored with fracture lines such that on piercing with a needle it readily fractures into components. Plastics and ceramics are examples of suitable rigid materials. Both of these types of dividing material provide a large opening between the first and second compartments, allowing quick mixing of the contents of the compartments. Alternative dividing materials include metal foils (e.g. aluminum foil) which may be coated with plastic.

The dividing material should be impermeable to water and the analyte to avoid leakage between the two compartments of the calibration chamber. In one embodiment, one surface of the dividing material is metallised to assist in preventing water diffusion. The metallised surface is typically in contact with the second compartment which is preferably under an inert gas atmosphere.

In order to speed up mixing of the contents of the first and second compartments (e.g. dissolution of a solid analyte into the water or aqueous solution), physical mixing of the calibration chamber, e.g. agitation or ultra-sonic mixing may be used or alternatively chemical additives that effervesce can be added to the calibration chamber to provide mixing. Particular embodiments for mixing the contents of the compartments are described below.

Once the contents of the two compartments are mixed, a second calibration solution is provided having a greater concentration of analyte than the first calibration solution. The sensor output from a reading taken on this solution therefore provides a second calibration point. This, along with a predetermined calibration algorithm, enables a calibration curve to be generated and the sensor to be calibrated. The skilled person would be familiar with appropriate algorithms for calibration of any particular type of sensor.

Typically, the calibration is carried out by connecting connection 8 of the sensor to a monitor adapted for continuous measurement of the sensor output. Thus, as soon as the sensor is exposed to the first compartment of the calibration chamber and the monitor connected and switched on, a first reading can be taken. Rupture or breakage of the dividing material is then carried out and the monitor will continually record the sensor output during mixing of the analyte source with the water or aqueous solution of the first compartment. The second reading is taken when the sensor output reaches a plateau due to mixing being complete. This can generally be achieved within about 2 minutes from the start of the calibration process.

In an automated process, one or more of the steps of exposing the sensor to the first compartment and removing or breaking dividing material 11 may be machine-driven. A stepper motor or a stepper motor attached to a lead screw may be used in this regard.

Invasive sensors typically operate in a temperature range of 35-39 C. However, calibration is normally carried out at room temperature. Many sensors are sensitive to temperature variation, in which case a calibration curve generated at room temperature will be shifted to a different set of values at, say, 37 C. The present invention provides two techniques by which this difficulty can be avoided.

A sensor will typically contain a temperature sensor, such that the temperature at which calibration is carried out can be determined. If the shift of the calibration curve with temperature for any particular sensor is known, following generation of the calibration curve as described above the curve can be shifted as necessary to account for the difference in temperature from that measured by the sensor during calibration to 37 C. Alternatively, a heating element (14 in FIG. 3a) may be provided to increase the temperature within the calibration chamber to 37 C prior to calibration. The temperature sensor within the sensor 1 can be used to monitor the actual temperature during calibration.

A number of alternative embodiments of the invention are described below. Each of these embodiments is the same as the first embodiment, except as particularly described.

Embodiment 2

Figure 4:
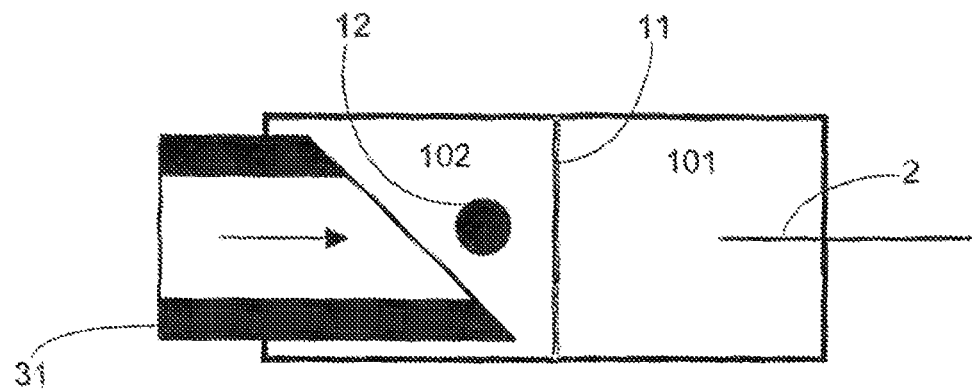
FIGS. 4 to 8 depict alternative embodiments of the calibration chamber of the invention.

An alternative embodiment of the calibration chamber is depicted in FIG. 4. In this embodiment, the first calibration compartment 101 contains water or an aqueous solution. The tip 2 of the sensor is here depicted within the first compartment, but can equally be provided outside the first compartment, or sealed from the first compartment. The second compartment 102 contains the analyte 12. In this embodiment, the dividing material 11 is broken by movement of needle 31 in the direction of the arrow through the dividing material. This can be achieved, for example, by depression of a plunger attached to needle 31, either manually or by an automated process.

The needle is here of substantially the same circumference as the second compartment, such that the analyte is pushed through the dividing material into the first compartment, aiding mixing.

Embodiment 3

Figure 5:
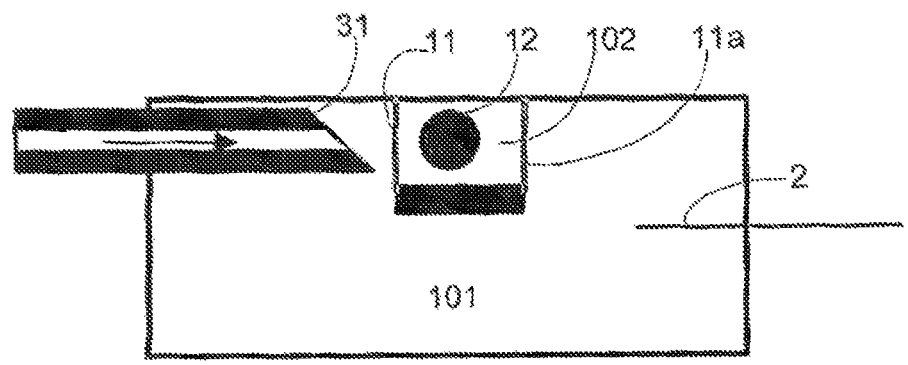

FIG. 5 depicts an embodiment in which the second compartment 102 has two dividing materials 11, 11a separating it from the first compartment 101. Movement of needle 31 from left to right in the direction of the arrow depicted in FIG. 5 causes first dividing material 11 to break or rupture exposing analyte 12 to the contents of the first compartment. Further movement of needle 31 in the same direction then causes dividing material 11a to break or rupture. This firstly has the effect of pushing analyte 12 into the first compartment 101, and secondly enables liquid present in the first compartment to flow through the second compartment. This aids mixing of the analyte 12 with the liquid in the first compartment.

Embodiment 4

Figure 6:
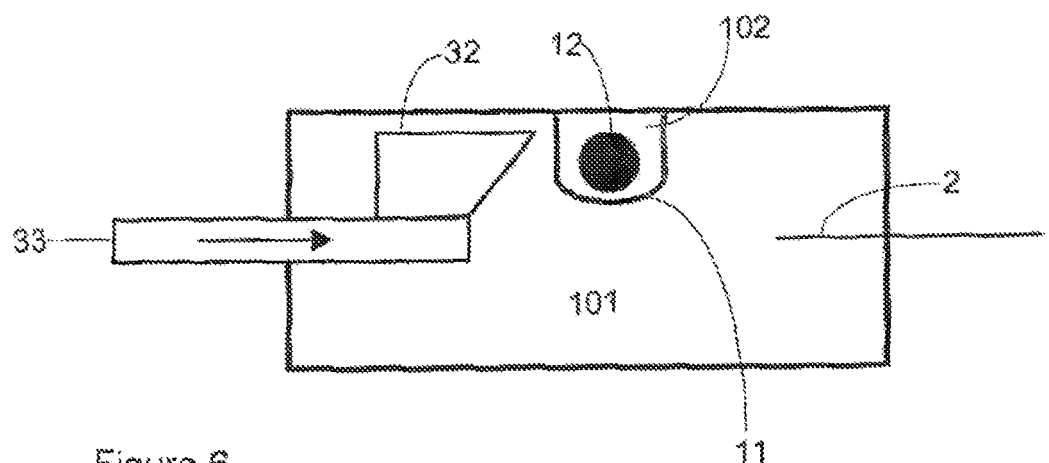

An alternative means of breaking dividing material 11 is depicted in FIG. 6. This embodiment includes a blade 32 attached to a plunger 33. The second compartment 102 is formed by a pouch of dividing material 11 attached to the wall of the first compartment 101. Movement of blade 32 in the direction of the arrow cuts through dividing material 11 thus exposing analyte 12 to the content of the first compartment. In this embodiment the walls of the second compartment are largely removed by movement of the blade, so mixing of the analyte and aqueous solution of the first compartment is improved.

Embodiment 5

Figure 7:
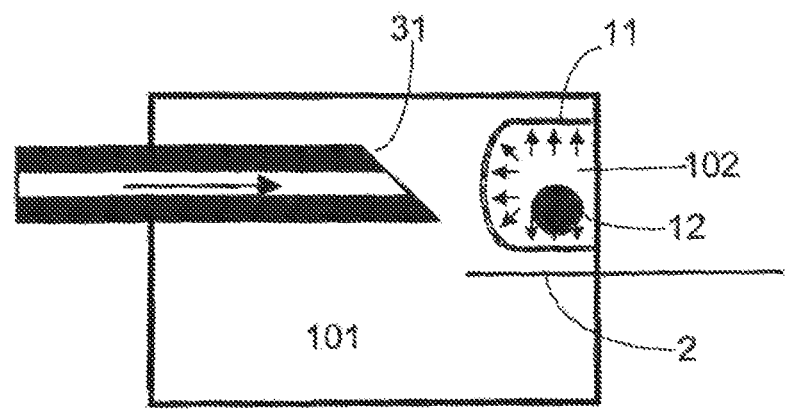

A fifth embodiment is depicted in FIG. 7. In this case the dividing material 11 is one which will rupture when pierced by the needle 31. For example, the dividing material may be a plastic-laminated foil, e.g. plastic-laminated aluminum foil. In this embodiment the second compartment 102 is maintained under pressure so that when the needle pierces the dividing material, the analyte 12 bursts out of the second compartment into the first compartment.

Embodiment 6

Figure 8:
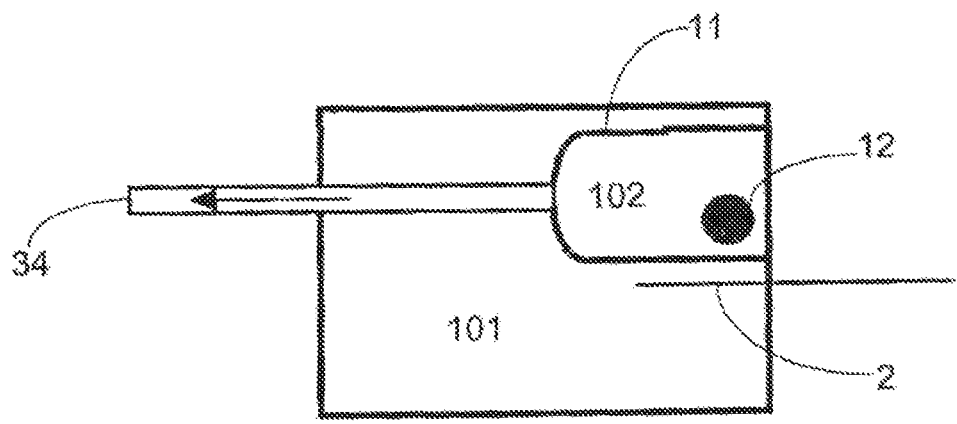

A sixth embodiment of the invention is depicted in FIG. 8. In this case the dividing material 11 is a release seal (e.g. a polyolefin) which is attached to arm 34. Movement of arm 34 in the direction of the arrow peels away the release seal thus exposing the analyte 12 to the aqueous solution of the first compartment.

Embodiment 7

A preferred calibration will include three calibration points in order to provide a better fit in the calibration curve. To provide three calibration points, three separate calibration solutions having different concentrations of analyte are needed. Embodiment 7 and those described below refer to 3 point calibrations. However, where appropriate, features of these systems may be used in two-point calibrations, or alternatively in four or more point calibrations.

Figure 3B:
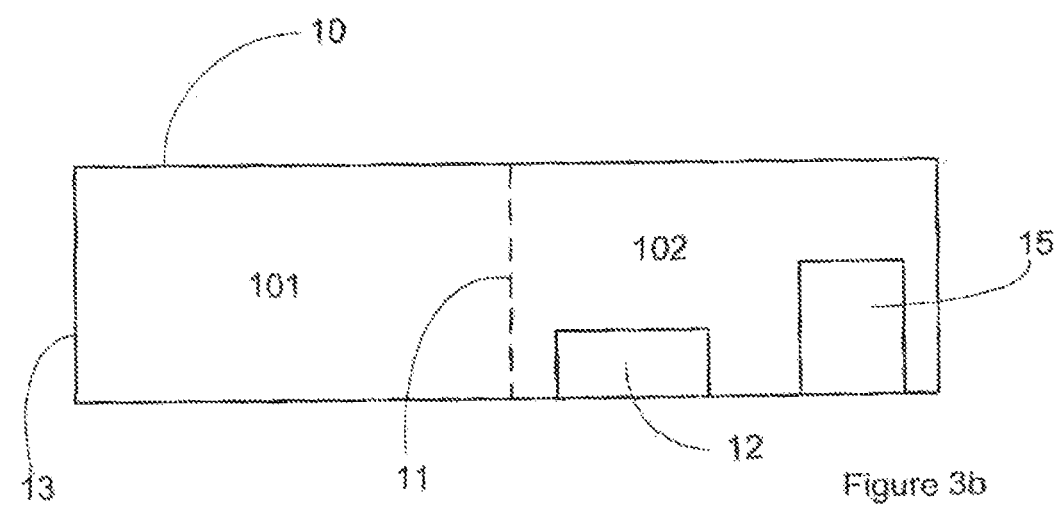

A preferred embodiment of the calibration chamber is depicted in FIG. 3b. In this embodiment a three-point calibration is achieved by incorporating a second source of analyte 15 in the form of a slow release capsule, into the second compartment. On rupture/breakage/removal of the dividing material 11, the slow release capsule will contact the water or aqueous solution of the first compartment and slowly dissolve.

The slow release capsule is designed such that its contents are released only after the second reading, corresponding to the second calibration solution, has been taken. Thus, a monitor detecting sensor output will observe a first increase in analyte concentration as the first analyte source dissolves, followed by a second distinct increase in analyte concentration as the second source of analyte dissolves following break-up of the slow release capsule.

Figure 9A:
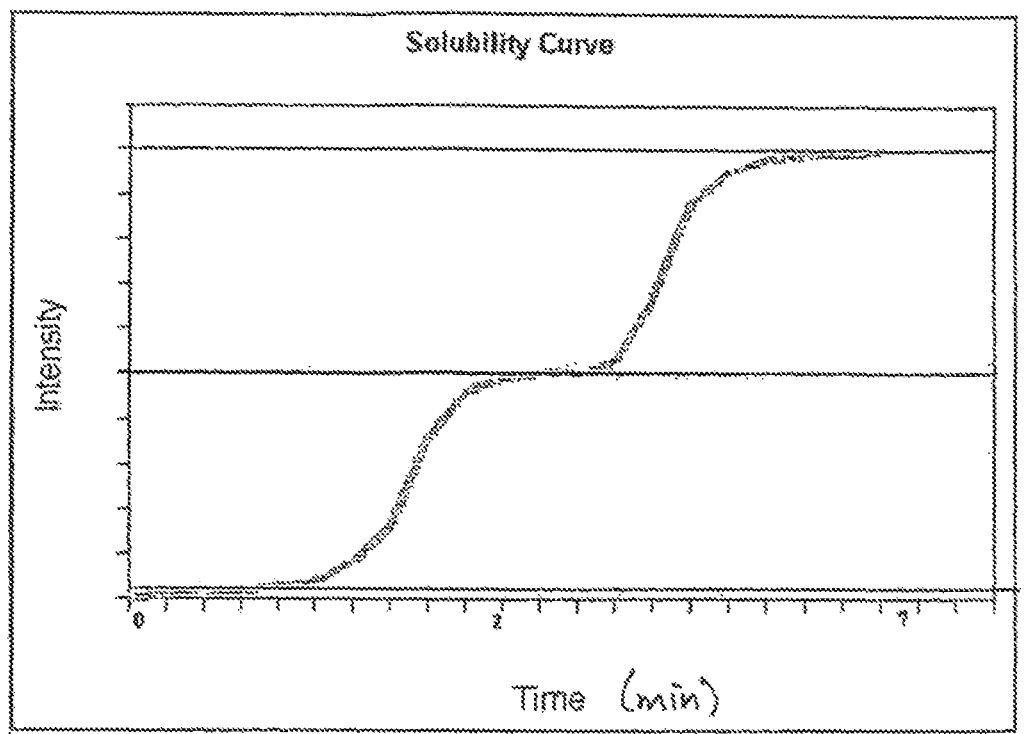
FIGS. 9a and 9b depict a typical solubility curve and calibration graph for a three-point calibration of a glucose sensor.
Figure 9B:
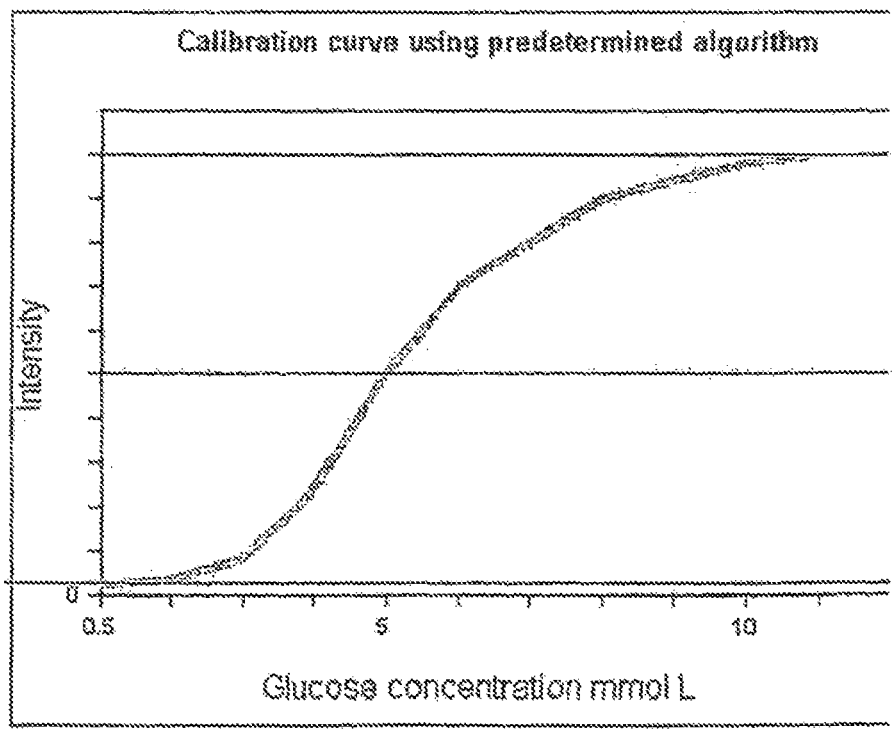

A typical solubility curve for such a calibration chamber is depicted in FIG. 9a. At time t=0 a first reading is taken corresponding to the first calibration solution. The dividing material is then ruptured/broken and the concentration of analyte is seen to increase until a plateau is reached at approximately t=2 minutes. A second reading is taken at this point corresponding to the second calibration solution. The slow release capsule is then seen to begin to release its contents and the concentration again increases until a plateau is reached at about t=5 minutes. A third reading is taken corresponding to the third calibration solution. This embodiment thus enables a more accurate calibration curve (FIG. 9b) to be generated. As the skilled person will appreciate, four or more point calibrations could be carried out in a similar manner simply by including further sources of analyte contained within further slow release capsules. By appropriate design of the release time of the slow release capsules, four or more separate calibration points can be generated.

Any appropriate slow release capsule may be used in this embodiment. In order to avoid excessively long calibration times, capsules which dissolve in the range of from about 1 to 10 minutes, preferably about 2 to 5 minutes, are preferred. Polyethylene oxide capsules are examples of suitable materials. The precise release time of the capsule can be controlled by variation of the thickness of the capsule in a manner which is well known in the art.

The skilled person would be able to determine suitable concentrations of analyte for the first, second and optional third or further calibration solutions. Typical concentrations should include zero (first analyte solution) and concentrations at the upper and lower end of those which are likely to be measured by the sensor. In the example of calibration of a glucose sensor for use with intensive care patients, a first calibration solution typically has a zero concentration, whilst the second and third calibration solutions typically have concentrations of, for example 5 mmolL$^{-1}$ and 10 mmolL$^{-1}$ respectively. Alternative concentrations could, however, be selected depending on the type and end use of the sensor. The volume of water or aqueous solution in the first compartment, and the amount of analyte contained in the first and optionally second and further sources of analyte should be chosen according to the desired final concentrations of the calibration solutions.

Embodiment 8

Figure 3C:
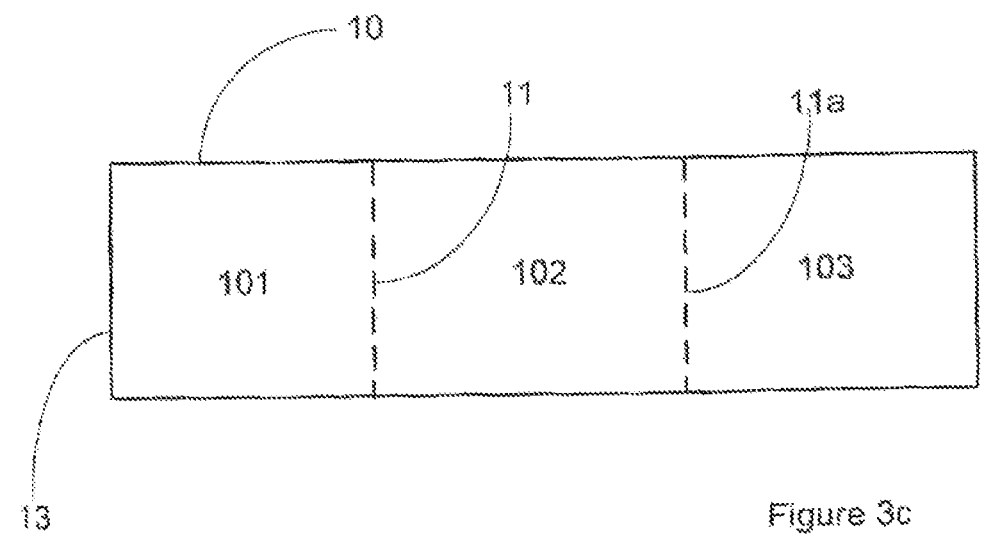

An alternative embodiment of the calibration chamber is depicted in FIG. 3c. In this embodiment, three compartments, 101, 102 and 103 are present. A dividing material 11, 11a separates each compartment. This embodiment provides a three point calibration by a different means. Following taking of the first reading, the first dividing material 11 is ruptured/broken/removed as discussed in other embodiments, the contents of first and second compartments are mixed and a second calibration solution is obtained. A second reading is then taken. Subsequently, the second dividing material 11a is ruptured/broken/removed allowing the contents of compartment 103 to mix with the second calibration solution. Compartment 103 contains a second source of analyte, thus providing a third calibration solution having a higher concentration of analyte than the first or second calibration solutions. A third reading can be taken and a calibration curve generated. This embodiment is appropriate for carrying out a three point calibration where the first and second sources of analyte are concentrated solutions of the analyte or the analyte in solid form.

Embodiment 9

Figure 10:
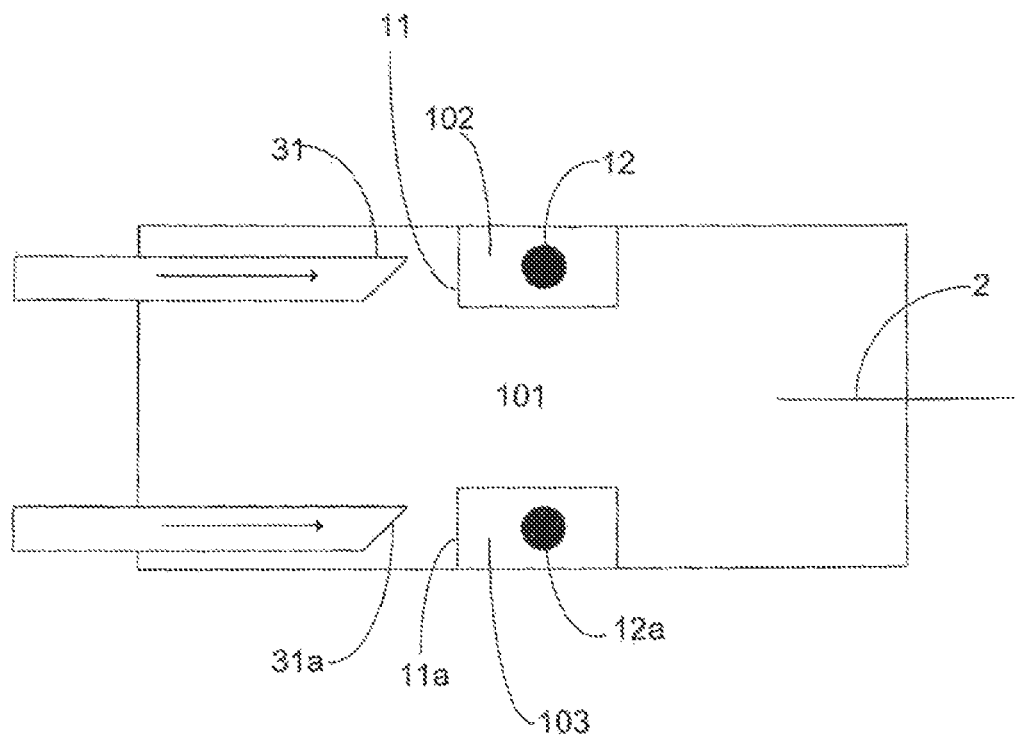
FIGS. 10 to 14 depict calibration chambers of the invention which provide a three point calibration.

FIG. 10 depicts an alternative three point calibration system containing three separate chambers 101, 102 and 103. This embodiment is the same as embodiment 8 above, except as described here. In this case, dividing material 11 of the second compartment 102 is pierced by needle 31. Mixing of the contents of compartments 101 and 102 provides a second calibration solution. A reading of the sensor output is taken once mixing is complete. The dividing material 11a of the third compartment 103 is then pierced by needle 31a. This causes analyte 12a to mix with the second calibration solution to provide a third calibration solution with a higher analyte concentration. The third reading of the sensor output can be taken once mixing is complete.

Figure 11:
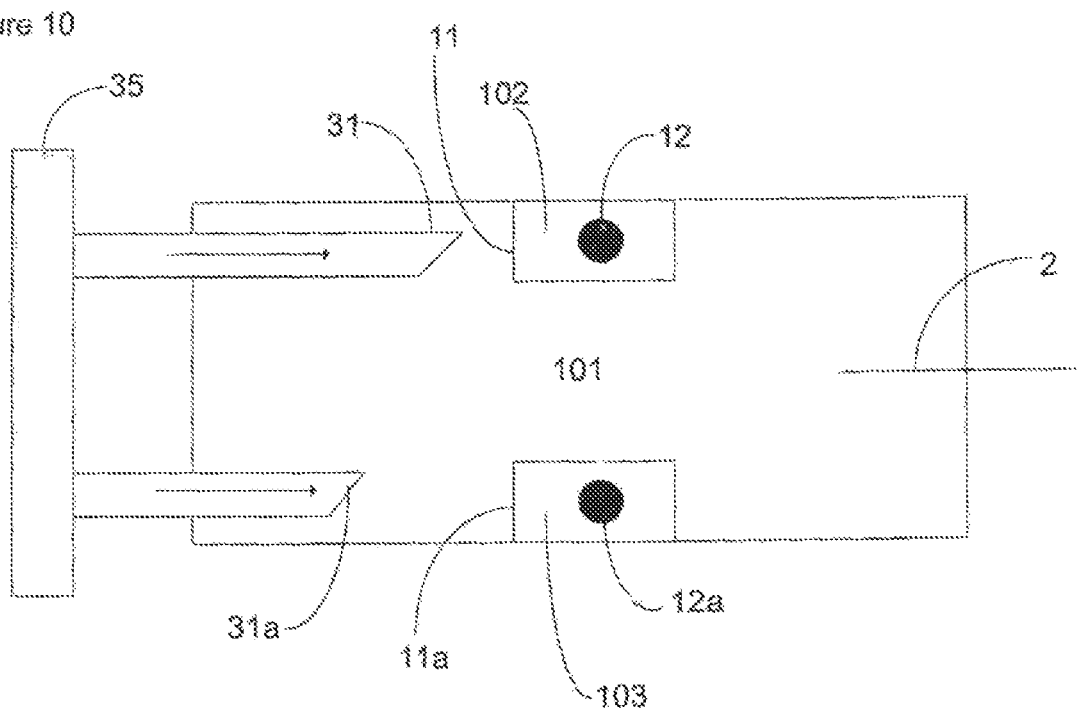

FIG. 10 depicts two simple needles piercing compartments 102 and 103. However, variations on the depicted embodiment can be provided, in which the second and third compartments are broken or ruptured in a different manner. For example, any of the features described in embodiments 2 to 6 may be utilized. Alternatively, a single plunger 35 may be provided to control movement of both needles 31 and 31a as shown in FIG. 11. In this embodiment, needle 31 is positioned closer to the compartment 102 than needle 31a is to compartment 103. In this way, movement of the plunger to a first "stop position" causes needle 31 to pierce breakable material 11, and subsequent movement of the plunger to a second "stop position" causes needle 31a to pierce breakable material 11a.

In a further variation a single needle 31 may be provided which can be controlled to pierce both of compartments 102 and 103 at the appropriate time. For example, needle 31 can be used to pierce dividing material 11 of compartment 102 by moving in the direction of the arrow and subsequently be withdrawn from that compartment. The needle can then be moved so that it is in line with the third compartment (e.g. by sliding the needle, or by rotating an axle to which the needle is attached) and again be moved in the direction of the arrow so that the dividing material 11a of the third compartment is pierced.

Embodiment 10

Figure 12:
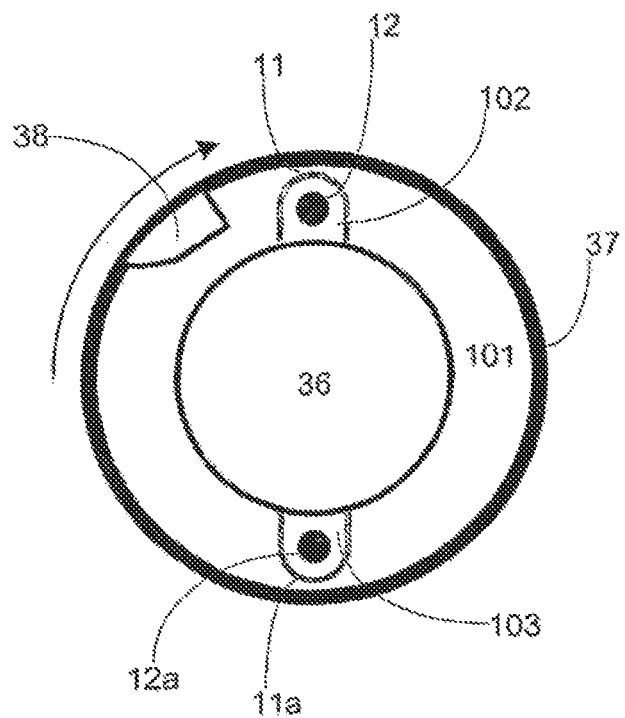

A rotary embodiment of the invention is depicted in FIG. 12. In this embodiment the calibration chamber contains an inner cylinder 36 and an outer cylinder 37 which can rotate with respect to one another. The first compartment 101 containing the first calibration solution is located between the inner and outer cylinders. Second and third compartments 102 and 103 are provided, each containing a source of analyte 12, 12a. Each of the second and third compartments is formed from a pouch of dividing material 11, 11a attached to the inner cylinder 36. A blade 38 is fixed to the outer cylinder. In a variation on this embodiment the blade could be attached to the inner cylinder and the second and third compartments attached to the outer cylinder.

Movement of the outer cylinder with respect to the inner cylinder in the direction of the arrow will cause the blade to break or rupture the second compartment 102. Analyte 12 mixes with the first calibration solution to provide a second calibration solution and a reading of sensor output can be taken. Further movement of the outer cylinder in the same direction will cause the blade to break or rupture the third compartment 103, causing mixing of analyte 12a with the second calibration solution, and thus providing a third calibration solution.

Embodiment 11

Figure 13:
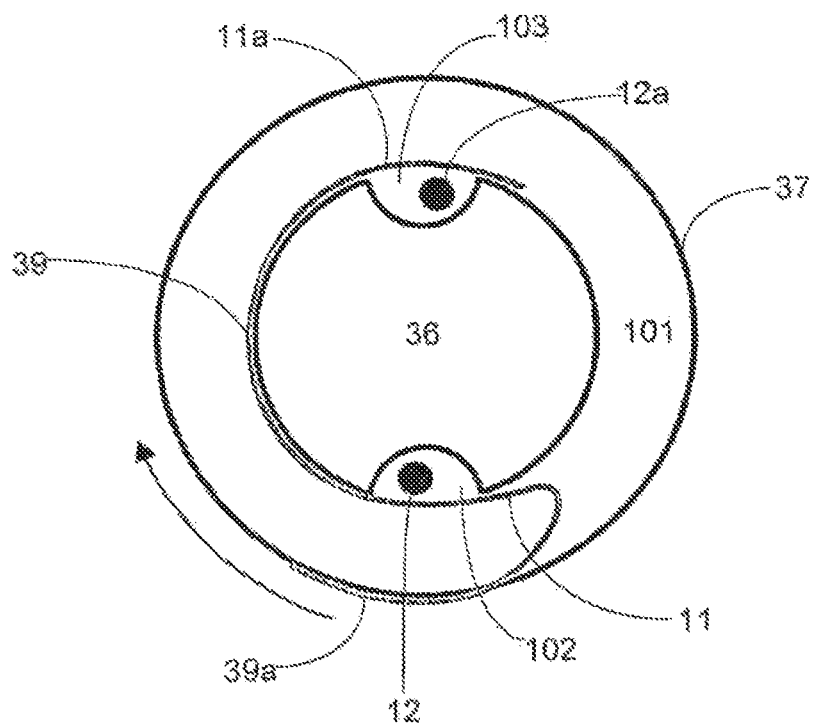

Embodiment 11, depicted in FIG. 13, is a variation of the rotary embodiment 10, but involves accessing the second and third compartments 102 and 103 by peeling away a seal 39. The first compartment 101 is located between an inner cylinder 36 and an outer cylinder 37. Second and third compartments containing a source of analyte 12, 12a are provided in the form of recesses in the inner cylinder. Each recess is sealed from the first compartment by seal 39 which seals the second compartment at 11 and seals the third compartment at 11a. The seal also extends to the outside of the calibration chamber at 39a. Pulling on the seal at 39a in the direction of the arrow will cause the seal to be broken on the second compartment 102 enabling analyte 12 to mix with the first calibration solution in the first compartment and thus providing a second calibration solution. A reading of sensor output is then taken. Further pulling on the seal 39a in the same direction will ultimately expose analyte 12a contained in the third compartment thus providing a third calibration solution.

As depicted here, a single seal 39 may be provided which seals both of compartments 102 and 103. Alternatively, however, two separate seals for each separate compartment may be provided.

Embodiment 12

Figure 14:
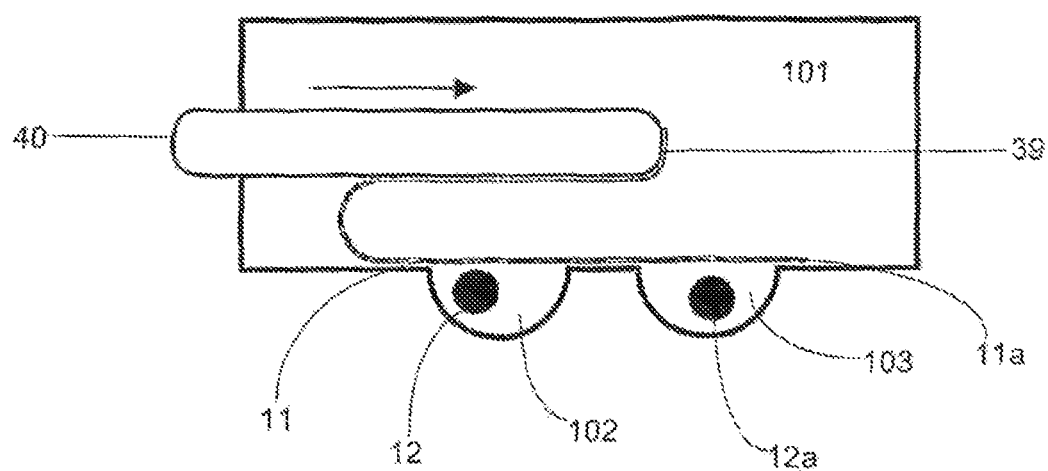

A variation on embodiment 11 is depicted in FIG. 14. In this embodiment a seal 39 is provided which forms a seal between the first and second compartments (101/102) and between the first and third compartments (101/103). The seal is here attached to a plunger 40. Movement of the plunger 40 in the direction of the arrow first exposes analyte 12 in the second compartment by peeling away portion 11 of the seal. In a subsequent movement of the plunger in the same direction, analyte 12a is exposed by peeling away portion 11a of the seal.

Mixing of Calibration Solutions

As discussed above, it is useful to provide means for mixing the one or more sources of analyte with the first calibration solution. Mixing not only helps to speed up the calibration process, but also ensures that the entirety of the source of analyte is dissolved in the calibration solution. This is important in providing an accurate calibration.

Figure 15:
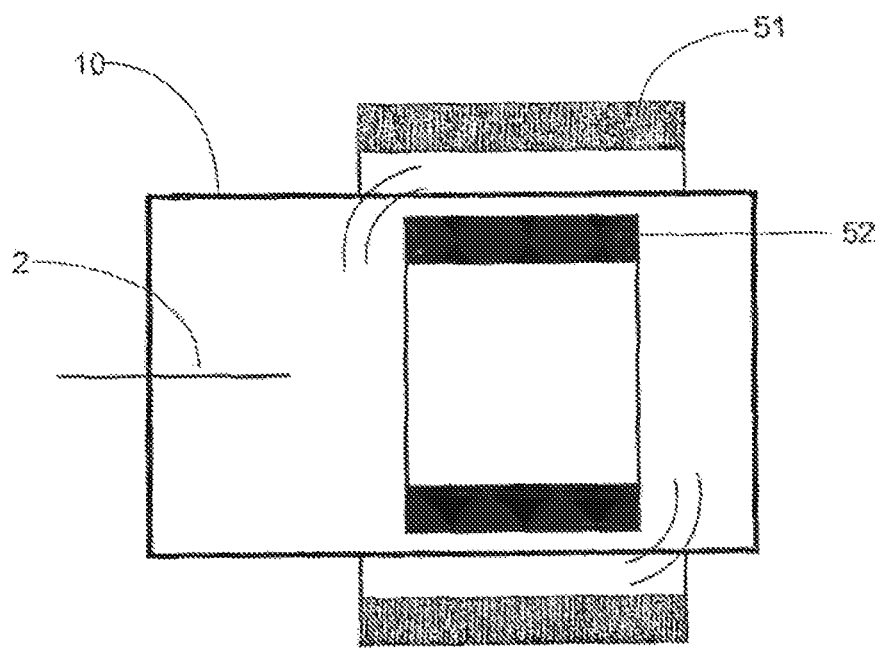
FIGS. 15 to 18 depict various means by which the contents of the calibration chamber can be mixed.

A number of different mixing arrangements are provided, including mechanical means, magnetic or electromagnetic and ultra-sonication. In one particular embodiment, depicted in FIG. 15, an electromagnet 51 is provided around the calibration chamber 10 and a moveable magnetic paddle 52 is provided within the chamber. Movement of the electromagnetic field generates movement of the paddle and causes mixing of the contents of the chamber.

Figure 16:
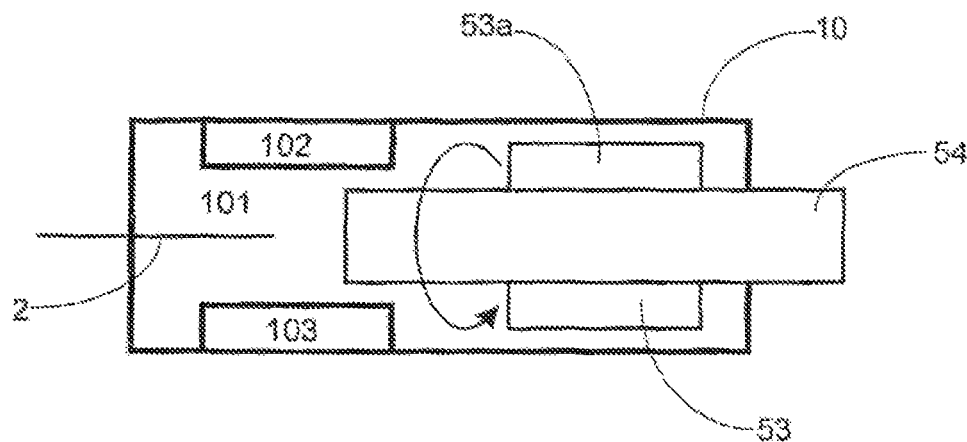

Alternatively, a mechanically operated paddle can be used, for example by attaching rotating fins or a propeller to a rod extending out of the calibration chamber. A device incorporating rotary fins is depicted in FIG. 16. In this embodiment, fins 53, 53a are provided on a central rod 54. Rotation of rod 54 causes mixing of the contents of compartment 101. This type of mixing technique can conveniently be used in combination with the rotary embodiments described above. For example in embodiment 10 described above, inner cylinder 36 can be provided with mixing paddles such as fins which extend into the first compartment 101, or a propeller can be attached to the end of the cylinder. Rotation of the inner cylinder with respect to the outer cylinder will cause the fins or propeller to rotate and to provide mixing of the contents of the first compartment 101.

Figure 17:
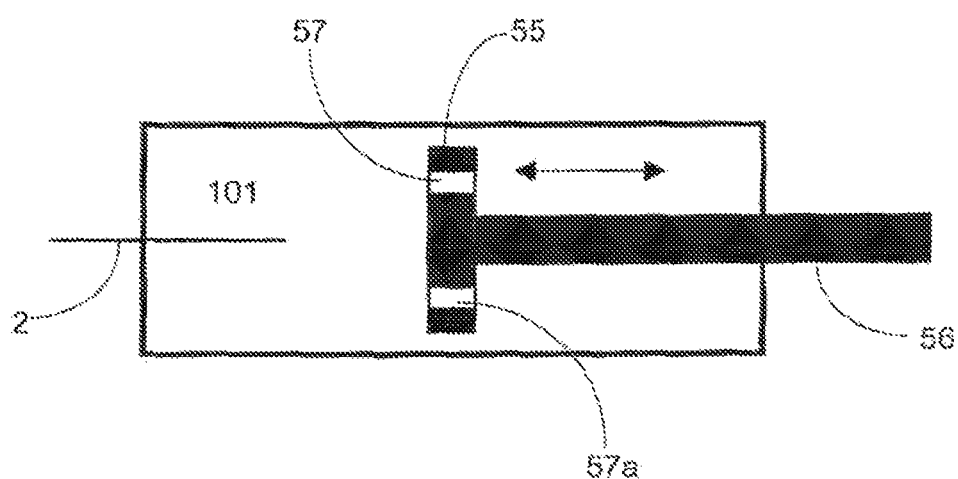

Mixing by a linear pump action is also envisaged. FIG. 17 shows a mixing technique which involves a piston 55 attached to rod 56. Holes 57, 57a are provided to allow movement of liquid through the piston. Movement of rod 56 reciprocally in the direction of the arrow provides mixing of the contents of compartment 101. Typically the piston fits into the calibration chamber relatively tightly, so that all, or almost all, of the liquid within the chamber must move through holes 57, 57a as the piston is moved through the chamber.

Figure 18A:
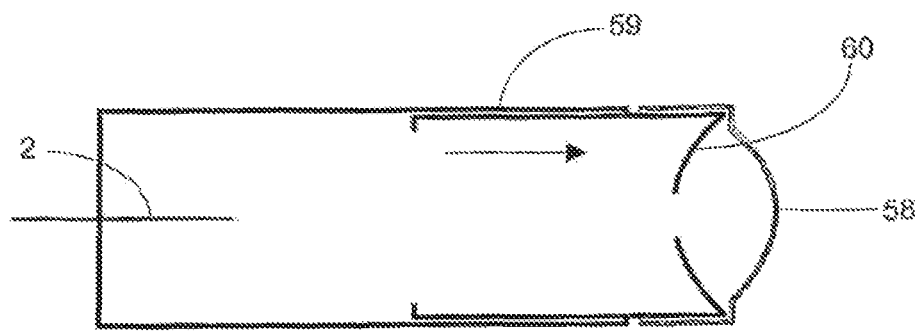

An alternative linear embodiment is shown in FIGS. 18a and b. This embodiment includes a flexible diaphragm 58 which forms one end of the calibration chamber. An inner sleeve 59 is also provided which typically has a concave end 60 which faces the flexible diaphragm. The concave end 60 is a solid wall having an opening. Reciprocal movement of the inner sleeve towards and away from the flexible diaphragm as shown in FIGS. 18a and b, causes liquid in the calibration chamber to be forced through the opening in concave end 60, causing mixing of the liquid.

Figure 18B:
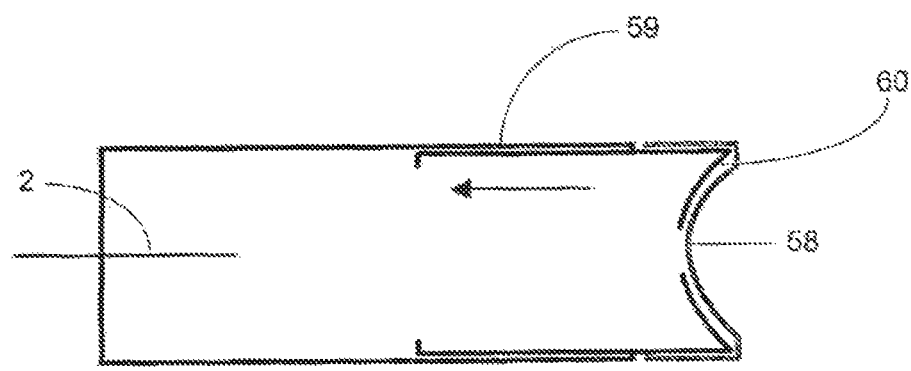

The linear mixing embodiments depicted in FIGS. 17 and 18 are suitable for use in combination with the embodiments in which a linear motion breaks or pierces dividing materials 11/11a. For example, in embodiment 9 above, needles 31, 31a may be mounted on a piston 55. Similarly, rod 40 of embodiment 12 may be attached to a piston 57 with a single rod 40 providing movement of the piston and seal 39. Similarly, embodiment 2 above may be fitted with a flexible diaphragm at one end of the chamber, and needle 31 may be mounted on an inner sleeve. Movement of needle 31 in a reciprocal direction would therefore not only provide breakage of dividing material 11, but would provide mixing by use of the inner sleeve/flexible diaphragm.

All or part of any embodiment can be used in conjunction with any other or part of any other embodiment, as appropriate.

Sensor Kit

The present invention provides a sensor kit which incorporates the sensor and calibration chamber of the invention as described above. The kit enables the sensor and calibration chamber to be provided to the user in sterile form and in a very easy to use format. Further, the sensor kit enables the user to easily maintain sterility of the calibration chamber and sensing region of the sensor during calibration.

Figure 19A:
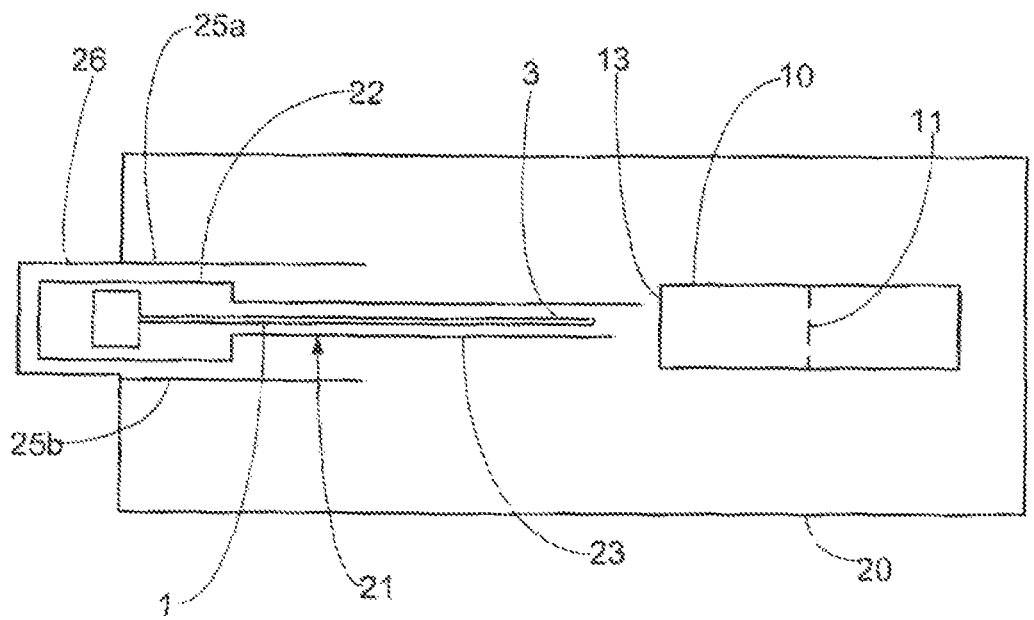
FIGS. 19a to 19c depict a sensor kit of the invention with the sensor in different positions within the kit (FIG. 19a=position for sterilisation.

An embodiment of the sensor kit is depicted in FIG. 19a. The kit includes a container 20 which accommodates the sensor 1 and calibration chamber 10. The calibration chamber 10 is typically fixed into a locked position within the container. The sensor is contained within sensor housing 21, including housing body 22 and piercing tip 23, for example a needle. The sensing region of the sensor is typically located within the piercing tip.

Figure 19B:
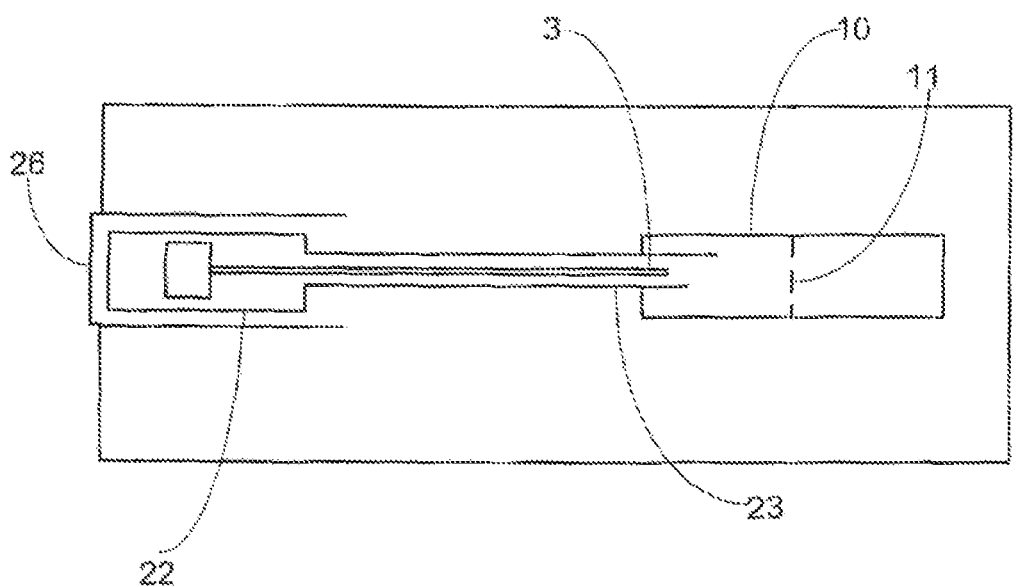

The sensor housing containing the sensor is movable laterally within the container, i.e. in a left/right direction as depicted in FIG. 19a. A guide channel formed by tracks 25a, 25b may be provided to ensure that movement of the sensor housing is restricted to this lateral direction and to limit free movement of the housing. In this way, the sensor housing can be moved such that the piercing tip penetrates the outer wall 13 of the calibration chamber and the sensing region of the sensor is inserted into the first compartment 101. FIG. 19b depicts the sensor in this latter position. The first calibration reading can be taken with the sensor and housing in this position.

The sensor housing is adapted to allow the first calibration solution to contact sensing region 3 when in the position shown in FIG. 19b. Typically, piercing tip 23 is a needle which allows liquids to enter the needle through its tip. However, other means of enabling the calibration solutions to penetrate the housing and contact the sensor may be provided.

Figure 19C:
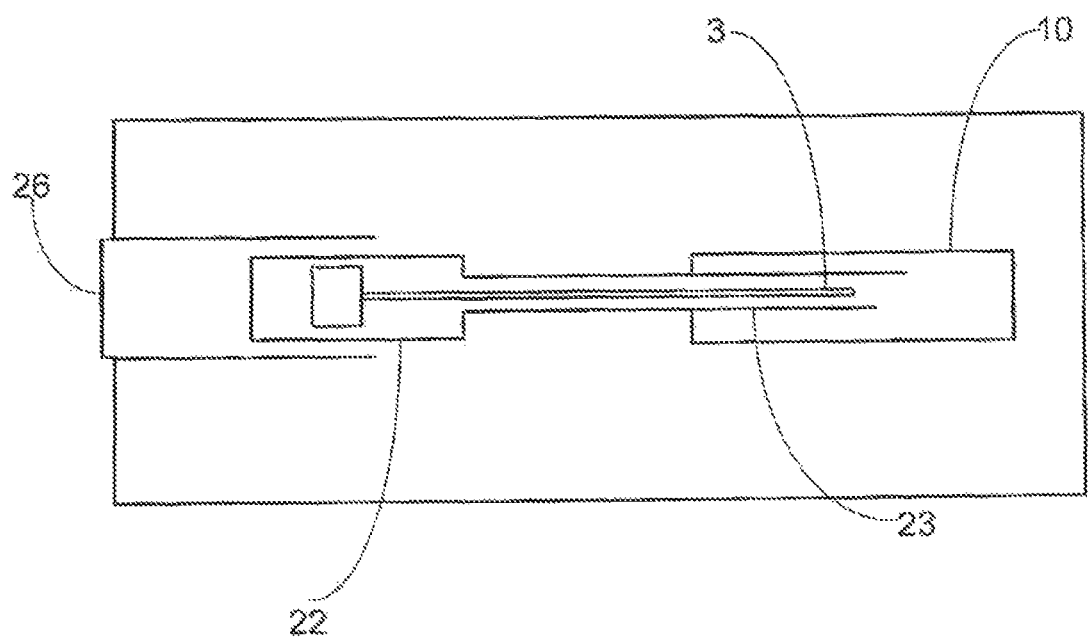

In one embodiment, further movement of the sensor housing will cause the dividing material 11 to be ruptured/broken so that the second, and optionally third, calibration reading(s) can be taken. FIG. 19c depicts the sensor after rupture/breakage of the dividing material by the piercing tip 23. In alternative embodiments, separate means for breaking or removing dividing material 11 are provided so that the second and optionally third calibration readings can be taken without further movement of the sensor housing.

The container 20 is typically sealed with a gas permeable lid (not depicted).

In order to maintain sterility of the device, it is advantageous to be able to move the sensor and sensor housing without breaking the seal of the container. In the embodiment depicted in FIG. 5a, this can be achieved by compressing compressible arm 26. This causes the sensor housing, containing the sensor to move laterally within the container. The compressible arm may be configured in the shape of a compressible bellows.

In an alternative embodiment of the sensor kit, a seal is provided between the sensor and the first compartment of the calibration chamber. In this embodiment, breaking the seal exposes the sensor to the first calibration chamber without necessitating movement of the sensor itself.

FIG. 20a shows a further embodiment of the sensor kit in cross-section. FIG. 20b is a perspective cut away view of the embodiment of FIG. 20a.

The sensor kit of FIG. 20 is similar to embodiment 12 illustrated in FIG. 14. Just like embodiment 12, the sensor kit of FIG. 20a comprises a plunger 40 to which a seal 39 (which seal 39 acts as the dividing material) is attached. Thus, linear movement of one part is effective to remove the water-impermeable dividing material and mix the contents of the first and second (and third) compartments.

The seal 39 extends from where it is attached at one end to the plunger 40 across an opening 101b of a sub-compartment 101a of the first compartment 101, across an opening 102b of the second compartment 102 into the first compartment 101 and across an opening 103b of the third compartment 103 into the first compartment 101 respectively.

The sensing region 3 of the sensor 1 is positioned within the first sub-compartment 101a.

First the kit is sterilised (see the sterilisation section below). A channel 75 is provided in fluid communication with the first sub-compartment 101a. This channel 75 allows the first sub-compartment 101a and the sensor 1 at least its sensing region 3 to be sterilised using ethylene oxide. The plunger 40 is then inserted into the container 20 and o-rings 76, 77 in combination with the plunger thereby seal channel 75.

The plunger 40 is moved far enough into the container 20 to pull the seal 39 away from the opening 101b of the first sub-compartment 101a. Thereby the first sub-compartment 101a and also the sensing part 3 of the sensor 1 are exposed to the inside of the container 20 which defines the first compartment 101.

To calibrate the sensor of FIG. 20 (which is done at the point of use) the plunger 40 is advanced further (preferably through a stepper motor/lead screw arrangement but this could also be done by hand) to expose the analyte contained in the second chamber 102 by peeling the seal 39 from over the opening 102b of the second chamber 102. Thus, the second 102 chamber becomes open to the inside of container 20 which defines the first compartment 101, as is the sensing part 3 of the sensor 1. Axially reciprocating movement of the plunger 40 between the position at which the seal 39 is removed from the second compartment 102 and a left hand position is effective to mix the solution in the container 20 (first compartment 101) to which the sensing part 3 is exposed. A calibration measurement may then be made.

The plunger 40 is then moved further to the right hand side (as illustrated) within the container 20 to pull the seal 39 from the opening 103b of the third compartment 103, thereby to expose the analyte in the third compartment 103 to the inside of container 20 (first compartment 101). Reciprocating axial movement of the plunger 40 then mixes the solution and a further calibration reading can be made.

Thus, as can be seen, the embodiment of FIG. 20 incorporates features of both embodiment 12 and the embodiment illustrated in FIG. 17.

Another embodiment is illustrated in FIG. 21. FIG. 21a is a cross-sectional view of the embodiment and FIG. 21b is a perspective view of a cut away of the embodiment. This embodiment uses a similar principle to that of embodiment 9, namely relative linear movement between a needle 31 and dividing material 11 which seals the contents of the second and third chambers 102, 103 from the contents of the first chamber 101. The relative linear movement is achieved through use of a lead screw.

In the embodiment of FIG. 21 the container 20 defines on its inner side a first compartment 101 just like the embodiment of FIG. 20. The first compartment 101 contains two needles 31, 31a, and an analyte housing which can be seen as a calibration chamber 10. The analyte housing 10 is splined to the container 20 and has an inner thread 82 which mates with a thread 81 of a lead screw 80. The lead screw 80 is coaxial with the container 20. Thus, rotation of the lead screw 80 can lead to linear movement of the analyte housing 10 within the sensor housing 20 without rotation of the analyte housing 10.

The sensor 1 is positioned within the lead screw 80 in a first sub-compartment 101a which, in the position shown in FIG. 21a, is open to the first compartment 101. During manufacture and sterilisation the lead screw 80 is positioned such that the chamber 101a is in fluid communication with channel 75 such that ethylene oxide sterilisation of at least the first sub-compartment 101a and the sensing part 3 can be performed. Then the lead screw 80 is pushed further into the compartment 20 so that o-ring 76 moves into the chamber 101 and o-ring 77 seals the chamber 101a from the channel 75. A snap fitting 88 can be provided to ensure that the lead screw 80 cannot be withdrawn from the sensor housing 20.

The analyte housing 10 contains the second compartment 102 and the third compartment 103. The second and third compartments 102, 103 are formed by through holes through the analyte housing 10. The through holes are in the axial direction and are sealed from the compartment 101 by water-impermeable dividing material 11 on each side.

In order to calibrate the device the lead screw 80 is rotated (preferably by an electric motor such as a stepper motor) so that the analyte housing 10 moves linearly within the container 20 (and of course the analyte housing 10 does not rotate because it is splined to the container 20). In order to calibrate the lead screw 80 is rotated such that the analyte housing 10 moves either left or right. Movement in the left direction will result in the needle 31a piercing the material 11 and thereby releasing the analyte contained in second compartment 102 into the first compartment 101. Reciprocal movement of the analyte housing through rotation of the lead screw 80 can then mix the solution. A calibration measurement may then be made. Movement of the analyte housing 10 to the right hand side through rotation of the lead screw 80 can then be used for piercing of the material 11 on one or each side of the third compartment 103 by needle 31. This releases the analyte in the third compartment 103 into the first compartment 101. Further rotation in both directions of the lead screw 80 results in mixing of the solution due to the axial reciprocal movement of the analyte housing 10 within the first compartment 101. A final calibration measurement may then be made.

Another embodiment of a sensor kit is illustrated in FIG. 22. FIG. 22a is a cross-sectional view and FIG. 22b is a perspective view of a cut out of the embodiment. FIG. 22c is a perspective view of a lead screw nut. In FIGS. 22a and b the position of the various components is illustrated such that the second compartment 102 is already open to the first compartment 101 which is defined by the container 20, i.e. in a position at which a calibration reading can be made.

The embodiment of FIG. 22 makes use of rotation to generate linear motion which is harnessed to remove a seal 39 from between compartments.

The analyte housing 10 is in the form of a tube and contains the sensor 1 which has its sensing part 3 in a first sub-compartment 101a which is open to the first compartment 101 through opening 101b. The analyte housing 10 also comprises a second compartment 102 and a third compartment 103 both of which are sealed by a seal 39 which acts as the dividing material.

The seal 39 may also extend to cover the opening 101b. Particularly in that case a channel 75 is provided for sterilisation of the sensor with ethylene oxide.

After sterilization a cap 90 is inserted into the container 20. The cap 90 is sealed with o-ring 91 to the container 20 thereby to seal the first compartment 101 which is defined by the inner walls of the container 20. The channel 75 is also sealed by the cap 90.

The cap 90 is splined to a lead screw 80 which comprises a coarse thread 81. The thread 81 of the lead screw 80 mates with the thread 84 of a lead screw nut 83 which is illustrated in more detail in FIG. 22c.

The thread 84 of the lead screw nut 83 is formed on a flexible arm 85 of the lead screw nut 83. This means that during rotation of the lead screw 80 in a first direction the thread 84 of the lead screw nut 83 mates with the thread 81 of the lead screw 80 thereby to move the lead screw nut in a linear direction (rightwards as illustrated). When the lead screw 80 is rotated in the opposite (second) direction, because of the shape of the thread 84 and that the fact that it is mounted on the flexible arm 85, the flexible arm 85 is bent so that the lead screw 80 can rotate without moving the lead screw nut 83. In order to ensure that, due to friction for example, the lead screw nut 83 does not rotate on rotation of the lead screw 80 in the second direction, resilient snap fitting arms 86 are provided which locate into recesses in the analyte housing 10 at the appropriate position of the lead screw nut 83 explained below.

An end of the seal 39 is attached to the lead screw nut 83. Therefore, in order to remove the seal 39 from the opening 101*b*, such that the first sub-compartment 101*a* can be open to the first compartment 101, the lead screw 80 is rotated in the first direction such that the lead screw nut 83 moves to the right. If desired, the lead screw 80 can be rotated in the opposite (second) direction and the lead screw nut 83 will stay in place. During rotation of the lead screw, fins 53 attached to the lead screw 80 will mix the solution in the first compartment 101.

In order to expose the analyte in the second compartment 102 to the first compartment 101, the lead screw 80 is rotated in the first direction thereby to move the lead screw nut 83 further towards the right as illustrated. This movement is effective to pull the seal 39 from off the opening 102*b* of the second compartment 102. Rotation in the second direction of the lead screw 80 then results in mixing of the solution in the first compartment 101 with the analyte in the second compartment 102 through fins 53. The lead screw nut 83 stays in place due to the flexible arm 85 bending and thereby disengaging the thread 84 of the lead screw nut 83 from the thread 81 of the lead screw 80. The snap fittings arms 86 also aid in preventing the lead screw nut 83 from moving further towards the left hand side.

The above process is performed again to uncover the third compartment 103 and to mix the analyte from the third compartment 103 with the solution already contained in the first compartment 101.

FIG. 23 illustrates a final sensor kit. FIG. 23*a* is a cut out perspective view of a container 20 into which the analyte housing 10 is inserted. FIG. 23*b* is a perspective view of the analyte housing 10. The analyte housing 10 comprises the second compartment 102 and the third compartment 103. The container 20 defines the first compartment 101 by its inner walls.

The embodiment illustrated in FIG. 23 uses the principle of at least one rotating element to remove a seal 39 (dividing material) first from an opening of the second compartment 102 and from an opening of the third compartment 103. The principles used are similar to those illustrated in FIGS. 13 and 16 in that the peeling action of the embodiment of FIG. 13 is combined with the mixing action of the embodiment of FIG. 16.

At the point of manufacture, a solution release plug 98 is pushed into the container 20. This seals off a channel 75 which can be used for sterilization with ethylene oxide. Once the solution release plug 98 has been pushed into the container 20, solution flows through opening 101*b* and onto the sensor 1.

In the embodiment of FIG. 23, two rotating elements are used. A first rotating element 92 is driven, for example by a stepper motor but also possibly by hand. One end of a first seal 39 is attached to the first rotating element 92 and the other end covers the opening between the second compartment 102 and the first compartment 101. Rotating the first rotatable element 92 in a first direction is effective to pull the seal 39*a* off so that the first and second compartments 101, 102 are in fluid communication.

Further rotation of the first rotatable element 92 results in mixing of the solution in the first compartment 101 with the analyte contained in the second compartment 102 due to the presence of mixing fins 53 on the inner side of the first rotatable element 92. A calibration reading may then be made.

A second rotatable element 94 is also provided. The second rotatable element 94 is driven by drive lugs 93 positioned on the first rotatable element 92 only when the first rotatable element is driven in a second direction which direction is opposite to the first direction. This is because the drive lugs 93 of the first rotatable element interact with driven spring arms 95 of the second rotatable element 94. These driven spring arms 95 are shaped and sprung such that when drive lugs 93 move relative to them in the first direction the driven spring arms spring out of the way so that the second rotatable element 94 does not rotate. In order to ensure that the second rotatable element 94 does not rotate in the first direction, retention spring arms 96 are provided which engage with mating features on the container 20.

Thus, once the first calibration measurement has been made following rotation of the first rotating element 92 in the first direction, the rotatable element 92 is rotated in the second direction and this in turn drives the second rotatable element 94 in the second direction. This is effective to peel a seal 39*b* which covers the opening between the third compartment 103 and the first compartment 101. The seal 39*b* is attached at one end to the second rotatable element 94 and at the other end over the opening of the third compartment 103. Continued rotation in the second (or first) direction of the first rotatable element 92 results in mixing of the analyte from the third compartment 103 due to the presence of fins 53. A further calibration reading may then be made.

Sterilization

The kit of the invention is preferably provided in sterile form and the invention therefore also provides a method for sterilising the kit. The method involves the separate sterilisation of the calibration chamber, e.g. by heat or y-radiation, preferably by y-radiation. The calibration chamber should therefore be made of appropriate materials to avoid damage during such sterilisation techniques, for example degradable plastics should be avoided. Further, it is preferred that the analyte (first and optional further sources of analyte) is in solid form under inert gas atmosphere. This avoids contact of the analyte with water and oxygen during sterilisation and thus helps to prevent degradation of the analyte.

The kit is then assembled, by placing the sensor into the sensor housing and the sensor housing into container (e.g. into the channel within the container). The calibration chamber is also placed into its designated position in the container. The container is then sealed with a lid which is at least in part gas permeable and the entire kit is sterilised, preferably using ethylene oxide. The lid of the kit is at least partly gas permeable to allow ethylene oxide sterilisation to take place. Suitable materials for use as the lid include microporous polyethylene. As will be apparent to the skilled person, any part of the container other than the lid may form the gas permeable part, as long as ethylene oxide sterilisation can take place.

Many sensors for use in invasive applications, including the exemplified glucose sensor described above, include hydrophilic materials, for example hydrophilic immobilisation materials to immobilise the receptor. Since ethylene oxide can react with water, prior to ethylene oxide sterilization the sensor and other materials are preferably dried to remove traces of water.

The sealed and sterilized kit is then ready for calibration and can be provided to the user, e.g. a hospital, in this form. In a preferred embodiment, however, prior to supply of the kit to the user, the sensor is exposed to the first calibration compartment by breaking a seal between the calibration chamber and sensor or by moving the sensor from its initial position as depicted in FIG. 5*a*, to that depicted in FIG. 5*b*. The sensing region of the sensor is then immersed in water or aqueous solution. The sensor housing can be locked in this position by an appropriate locking mechanism if desired.

This embodiment minimizes the steps to be carried out by the user on receipt of the device. However, it has particular advantages in connection with sensors including a hydrophilic immobilisation material, such as the glucose sensor described above. Such sensors typically need to be hydrated for efficient use. Since the sensor must be dehydrated prior to ethylene oxide sterilisation, re-hydration of the sensor is required.

This can be achieved simply by exposing the sensor to the first calibration compartment so that the sensor is re-hydrated by the water or aqueous solution in the first compartment. The sensor is thus typically already fully hydrated on receipt by the user, and can be calibrated and used immediately.

The invention has been described with reference to various specific embodiments and examples. However, it is to be understood that the invention is in no way limited to these specific embodiments and examples.

The invention claimed is:

1. A method of calibrating a sensor in a sensor kit, the method comprising:
   exposing a sensing region of a sensor to a first compartment of a calibration chamber so that a first calibration solution is in contact with the sensing region;
   determining the sensor output for the first calibration solution;
   breaking a breakable dividing material of the calibration chamber, to form a second calibration solution comprising a mixture of the first calibration solution and a source of analyte, wherein the source of analyte is in solid form prior to breaking or removing the dividing material of the calibration chamber;
   determining the sensor output for the second calibration solution; and
   using the determined sensor output readings to calibrate the sensor.

2. The method of claim 1, wherein the source of analyte is stored in an inert gas atmosphere prior to breaking the dividing material of the calibration chamber.

3. The method of claim 1 wherein the first calibration solution is substantially free of analyte.

4. The method of claim 1, wherein the source of analyte comprises glucose.

5. The method of claim 1, which further comprises a step of mixing the second calibration solution prior to determining the sensor output for the second calibration.

6. The method of claim 1, wherein the calibration chamber comprises a third compartment containing a second source of the analyte, said third compartment being separated from the remainder of the calibration chamber by a second dividing material, and wherein said method comprises breaking or removing the second dividing material to form a third calibration solution comprising a mixture of the second calibration solution and the second source of analyte and determining the sensor output for the third calibration solution.

7. The method of claim 6, wherein the second source of analyte is in solid form.

8. The method of claim 6, further comprising mixing the third calibration solution prior to determining the sensor output for the third calibration solution.

9. The method of claim 1, wherein the sensing region of the sensor is exposed to the first compartment of the calibration solution by breaking or removing a seal which separates the sensor from the first compartment.

10. The method of claim 1, wherein the steps are automated.

11. The method of claim 1, further comprising sterilizing the calibration chamber prior to exposing the sensing region of the sensor to the first compartment of the calibration chamber.

12. The method of claim 1, wherein the calibration chamber is sterilized using γ-ray irradiation.

13. The method of claim 1, comprising (i) sterilizing the calibration chamber to provide a pre-sterilized calibration chamber, and (ii) inserting the pre-sterilised calibration chamber, sensor and sensor housing into a container, sealing the container and sterilising the container, sensor and sensor housing.

* * * * *